United States Patent
Conlan et al.

(10) Patent No.: US 10,406,124 B2
(45) Date of Patent: Sep. 10, 2019

(54) METHOD OF TREATMENT OF GYNECOLOGICAL CANCER WITH ANTI-RAGE ANTIBODIES

(71) Applicant: Swansea University, Swansea, South Wales (GB)

(72) Inventors: Robert Conlan, Swansea (GB); Deyarina Gonzalez, Swansea (GB)

(73) Assignee: Swansea University, Swansea (GB)

( * ) Notice: Subject to any disclaimer, the term of this patent is extended or adjusted under 35 U.S.C. 154(b) by 0 days.

(21) Appl. No.: 15/519,826

(22) PCT Filed: Oct. 21, 2015

(86) PCT No.: PCT/GB2015/053156
§ 371 (c)(1),
(2) Date: Apr. 17, 2017

(87) PCT Pub. No.: WO2016/063060
PCT Pub. Date: Apr. 28, 2016

(65) Prior Publication Data
US 2017/0246315 A1    Aug. 31, 2017

(30) Foreign Application Priority Data
Oct. 22, 2014 (GB) .................... 1418809.8

(51) Int. Cl.
| | |
|---|---|
| *A61K 31/138* | (2006.01) |
| *C07K 16/28* | (2006.01) |
| *A61K 39/395* | (2006.01) |
| *A61K 45/06* | (2006.01) |
| *A61K 47/68* | (2017.01) |

(52) U.S. Cl.
CPC ........ *A61K 31/138* (2013.01); *A61K 39/3955* (2013.01); *A61K 45/06* (2013.01); *A61K 47/6803* (2017.08); *A61K 47/6817* (2017.08); *A61K 47/6869* (2017.08); *A61K 47/6873* (2017.08); *A61K 47/6889* (2017.08); *C07K 16/2803* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 6,573,096 B1 * | 6/2003 | Chen ............... | C07K 14/70596 435/326 |
| 2010/0143349 A1 * | 6/2010 | Hufton ............... | C07K 16/2803 424/133.1 |
| 2011/0195924 A1 | 8/2011 | Logsdon et al. | |

FOREIGN PATENT DOCUMENTS

| | | |
|---|---|---|
| WO | WO 2005/081711 A2 | 9/2005 |
| WO | WO 2010/019656 A1 | 2/2010 |
| WO | WO 2012/109569 A1 | 8/2012 |

OTHER PUBLICATIONS

Diamanti-Kandarakis et al. Immunohistochemical localization of advanced glycation end-products (AGEs) and their receptor (RAGE) in polycystic and normal ovaries, Histochem. Cell Biol., 127, 581-589, 2007. (Year: 2007).*
Zicari et al., HCG modulates HMGB1 and RAGE expression in normal human endometrium and in endometrial cancer. Placenta 34 , p. A18, abstr. D10, 2013. (Year: 2013).*
Sevillano et al. Internalization of the Receptor for Advanced Glycation End Products (RAGE) is required to mediate intracellular responses. J. Biochem. 145, 21-30, 2009. (Year: 2009).*
Page et al. (Treatment of drug resistant ovarian cancer cells with daunorubicin antibody conjugates. Mol. Biol. Cell, 7, SUPPL., p. 77A, 1996. (Year: 1996).*
Stephan et al. Anti-cd22-MCC-DM1 and MC-MMAF conjugates: Impact of the assay format on pharmacokinetic parameters determination. Bioconj. Chem. 19, 1673-1683, 2008. (Year: 2008).*
Francisco et al. cAC10-vcMMAE, an anti-CD30-monomethyl auristatin E conjugate with potent and selective antitumor activity. Blood, 102, 1458-1465, 2003. (Year: 2003).*
Diamanti-Kandarakis et al., "Immunohistochemical Localization of Advanced Glycation End-Products (AGEs) and Their Receptor (RAGE) in Polycystic and Normal Ovaries," *Histochem Cell Biol.* 127:581-589, 2007.
Girón et al., "Sequencing of Two Alternatively Spliced mRNAs Corresponding to the Extracellular Domain of the Rat Receptor for Advanced Glycosylation End Products (RAGE)," *Biochem Biophys Res Commun.* 251:230-234, 1998.
Hsieh et al., "Expression Analysis of S100 Proteins and RAGE in Human Tumors Using Tissue Microarrays," *Biochem Biophys Res Comm.* 307:375-381, 2003.
Scales et al., "An Antimesothelin-Monomethyl Auristatin E Conjugate with Potent Antitumor Activity in Ovarian, Pancreatic, and Mesothelioma Models," *Mol Cancer Ther.* 13:2630-2640, 2014.
Sevillano et al., "Internalization of the Receptor for Advanced Glycation End Products (RAGE) is Required to Mediate Intracellular Responses," *J. Biochem.* 145:21-30, 2008.

(Continued)

*Primary Examiner* — Elly-Gerald Stoica
(74) *Attorney, Agent, or Firm* — Klarquist Sparkman, LLP

(57) ABSTRACT

A therapeutic agent comprising a cell binding agent which binds the Receptor for Advanced Glycation End (RAGE) products linked to an anti-cancer drug, for use in the treatment of gynaecological cancer, endometriosis or polycystic ovary syndrome. Novel cell binding agents, pharmaceutical compositions and methods are also described and claimed.

10 Claims, 16 Drawing Sheets
Specification includes a Sequence Listing.

(56) References Cited

OTHER PUBLICATIONS

Tse et al., "CR014-vcMMAE, a Potent Fully Human Monoclonal Antibody-Monomethylauristatin E Conjugated Drug Targeting Ovarian and Renal Cell Carcinoma," Abstract from Proceedings of the American Association for Cancer Research Annual Meeting, vol. 47, p. 275, 2006.
GB1418809.8 Search Report dated Jul. 3, 2015 (5 pages).
PCT/GB2015/053156 International Search Report and Written Opinion dated Mar. 24, 2016 (17 pages).

* cited by examiner

A = secondary control
B-F = TOV112D cells, internalisation after 60 min
G-K = Hec 1A cells, internalisation after 60 min

A

Figure 19 contd
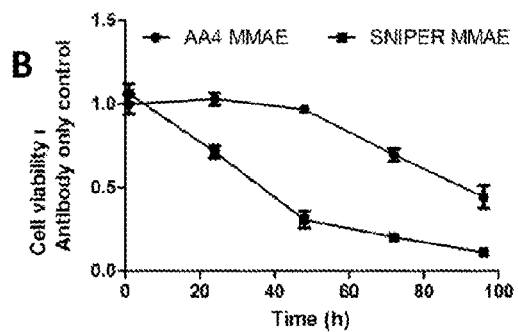
Figure 20
A                                          B
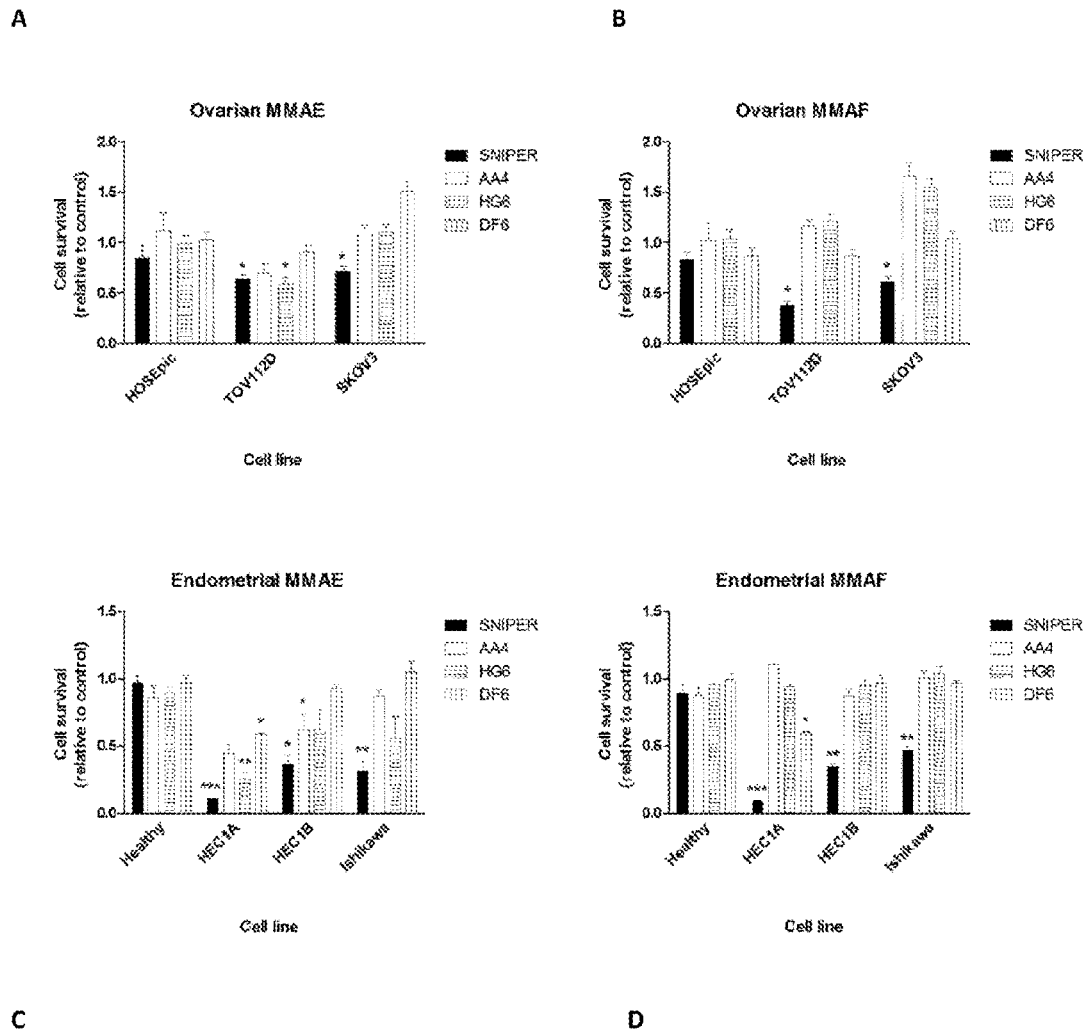
C                                          D

METHOD OF TREATMENT OF GYNECOLOGICAL CANCER WITH ANTI-RAGE ANTIBODIES

CROSS-REFERENCE TO RELATED APPLICATIONS

This application is a national stage application under 35 U.S.C. § 371 of PCT/GB2015/053156, filed Oct. 21, 2015, which claims benefit of British application GB 1418809.8, filed Oct. 24, 2014, which is incorporated herein by reference.

SEQUENCE LISTING

The Sequence Listing associated with this application is filed in electronic format via EFS-Web and hereby is incorporated by reference into the specification. The name of the text file containing the Sequence Listing is Replacement_Seq_List_CPG-00056_ST25.txt. The size of the text file is 58 KB, and the text file was created on Apr. 10, 2017.

The present application relates to therapeutic agents, in particular antibody-drug conjugates, useful in the treatment of proliferative disease, in particular gynaecological cancers or polycystic ovary syndrome, in which the receptor for advanced glycation end products (RAGE) protein exhibits altered expression compared to physiologically normal tissues. Certain of the agents are novel and form a further aspect of the invention, as well as pharmaceutical compositions comprising the agents, methods for preparing them and their use in therapy.

BACKGROUND OF THE INVENTION

The receptor for advanced glycation end (RAGE) products is a member of the immunoglobulin superfamily of cell surface molecules,[1] located on chromosome 6p21.3 at the major histocompatibility complex class III region.[2] Full length RAGE is 404 amino acids in length, comprising an extracellular domain, a single hydrophobic transmembrane domain and a short cytosolic tail. Ligand binding properties are provided by the extracellular domain, which can be divided into three functional regions; the V domain, C1 and C2 domains (FIG. 1 hereinafter).[3] An increasing number of ligands are known to bind RAGE including, advanced glycation end products (the receptors namesake), high-mobility group protein 1, and members of the S100 protein family.[4-7] Central to its role in an inflammatory responses, is the internalisation of RAGE following ligand binding, which is a key component of RAGE-mediated signal transduction.[8] Tissue distribution of RAGE under physiological conditions is limited, and with the exception of the lungs, expression is low.[9]

The up-regulation of RAGE expression is associated with a wide range of diseases, in particular in a range of inflammatory diseases such as diabetes and Alzheimer's disease.[4,14] There is also evidence linking RAGE to cancer progression in mice and humans[10-13].

Following the limited success of therapies which use monoclonal antibodies in the treatment of cancer, there has been some considerable interest in drug-antibody conjugates. The approach here is to attach to the antibodies, small molecule drugs, such as cytotoxins or other anti-cancer agents. The antibody acts as a targeting agent, carrying the drug directly to the tumour cell, and thus permitting discrimination between cancer cells and normal tissue. However, initial work has shown that the selection of appropriate targets is critical for effective therapies to be developed.

Humanised anti-RAGE antibodies and therapeutic agents comprising them are described for example in WO2010/019656. It is suggested that they may be useful in a wide range of diseases in which RAGE is implicated.

The applicants have found that RAGE is upregulated in a number of specific cancers, including in particular gynaecological cancers such as endometrial or ovarian cancer. Furthermore, they have found that this receptor can be effectively targeted by antibodies in complex with cytotoxic drugs, thereby producing useful anti-cancer effects.

SUMMARY OF THE INVENTION

According to the present invention there is provided a therapeutic agent comprising a cell binding agent which binds the receptor for advanced glycation end products (RAGE) linked to an anti-cancer drug, for use in the treatment of a proliferative disease selected from gynaecological cancer, endometriosis and polycystic ovary syndrome.

The cell binding agent is suitably one of, but without limitation to, an antibody or a binding fragment thereof, such as a Fab, Fab', F(ab)2, F(ab')2 and FV, VH and VK fragments; a peptide; an aptamer, a nanobody or other non-antibody affinity reagent. Antibodies may be monoclonal or polyclonal but in particular are monoclonal antibodies. Whilst the antibody may be from any source (murine, rabbit etc.), for human therapeutic use, they suitably comprise a human antibody or an antibody which has been partly or fully humanised.

The sequence of human RAGE is known, as well as a further twenty two variants including soluble RAGE (sRAGE). These are shown herein as SEQ ID NO 1 through SEQ ID NO 23, with full RAGE being SEQ ID NO 1 and sRAGE being SEQ ID No 2. The cell binding agent therefore is required to bind to an epitopic region of SEQ ID NO 1 or SEQ ID NO 2 or SEQ ID 3 or SEQ ID NO 4 or SEQ ID NO 5 or SEQ ID NO 6 or SEQ ID NO 7 or SEQ ID NO 8 or SEQ ID NO 9 or SEQ ID NO 10 or SEQ ID NO 11 or SEQ ID NO 12 or SEQ ID NO 13 or SEQ ID NO 14 or SEQ ID NO 15 or SEQ ID NO 16 or SEQ ID NO 17 or SEQ ID NO 18 or SEQ ID NO 19 or SEQ ID NO 20 or SEQ ID NO 21 or SEQ ID NO 22 or SEQ ID NO 23.

However, it is also known that RAGE is subject to protein ectodomain shedding.[15] In a particular embodiment of the invention, the cell binding agent of the complex of the invention binds a region of the ectodomain of RAGE which remains after any such shedding occurs. For example amino acids 317 to 344 of SEQ ID NO 1, herein denoted as SEQ ID NO 24. In this way, the activity of the agent may be maximised since it might be expected to continue to act, even after shedding. In particular therefore, the therapeutic agent of the invention comprises a cell binding agent which binds a residual extracellular fragment of RAGE remaining after shedding of the ectodomain. In a particular embodiment therefore, the cell binding agent binds to an epitopic region of SEQ ID NO 24.

In another embodiment, the therapeutic agent of the invention comprises a cell binding agent which binds a V-type domain of the RAGE, where the V-type domain is found at amino acids 23 to 116 of SEQ ID NO 1. In yet another embodiment, the therapeutic agent binds a domain of RAGE for which MAB11451 is specific.

In a particular embodiment, the anti-cancer molecule used in the therapeutic is a cytotoxin, such as a small molecule cytotoxin, a hormone, a cytokine/chemokine or other cell signalling molecule, or a nucleic acid and shall hereinafter be referred to as an 'anti-cancer drug.'

In particular, the anti-cancer drug is a cytotoxin that inhibits or prevents the function of cells and/or causes destruction of cells. Examples of cytotoxins include, but are not limited to, radioactive isotopes, chemotherapeutic agents, and toxins such as small molecule toxins or enzymatically active toxins of bacterial, fungal, plant or animal origin, including synthetic analogues and derivatives thereof. The cytotoxic agent may be selected from the group consisting of an auristatin, a DNA minor groove binding agent, a DNA minor groove alkylating agent, an enediyne, a lexitropsin, a duocarmycin, a taxane, a puromycin, a dolastatin, a maytansinoid and a *vinca* alkaloid or a combination of two or more thereof.

Other suitable anti-cancer drugs include topoisomerase inhibitors, alkylating agents (eg. nitrogen mustards; ethylenimes; alkylsulfonates; triazenes; piperazines; and nitrosureas), an antimetabolite (eg mercaptopurine, thioguanine, 5-fluorouracil), a mitotic disrupter (eg. plant alkaloids-such as vincristine and/or microtubule antagonists-such as paclitaxel), a DNA intercalating agent (eg carboplatin and/or cisplatin), a DNA synthesis inhibitor, a DNA-RNA transcription regulator, an enzyme inhibitor, a gene regulator, a hormone response modifier, a hypoxia-selective cytotoxin (eg. tirapazamine), an epidermal growth factor inhibitor, an anti-vascular agent (eg. xanthenone 5,6-dimethylxanthenone-4-acetic acid), a radiation-activated prodrug (eg. nitroarylmethyl quaternary (NMQ) salts) or a bioreductive drug or a combination of two or more thereof.

Non-limiting examples of chemotherapeutic agents include Auristatin, Erlotinib (TARCEVA®), Bortezomib (VELCADE®), Fulvestrant (FASLODEX®), Sutent (SU11248), Letrozole (FEMARA®), Imatinib mesylate (GLEEVEC®), PTK787/ZK 222584, Oxaliplatin (Eloxatin®), 5-FU (5-fluorouracil), Leucovorin, Rapamycin (Sirolimus, RAPAMUNE®), Lapatinib (GSK572016), Lonafarnib (SCH 66336), Sorafenib (BAY43-9006), and Gefitinib (IRESSA®), AG1478, AG1571 (SU 5271; Sugen) or combination of these.

The chemotherapeutic agent may be an alkylating agent-such as thiotepa, CYTOXAN® and/or cyclosphosphamide; an alkyl sulfonate-such as busulfan, improsulfan and/or piposulfan; an aziridine-such as benzodopa, carboquone, meturedopa and/or uredopa; ethylenimines and/or methylamelamines-such as altretamine, triethylenemelamine, triethylenephosphoramide, triethylenethiophosphoramide and/or trimethylomelamine; acetogenin-such as bullatacin and/or bullatacinone; camptothecin; bryostatin; callystatin; cryptophycins; dolastatin; duocarmycin; eleutherobin; pancratistatin; sarcodictyin; spongistatin; nitrogen mustards-such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide and/or uracil mustard; nitrosureas-such as carmustine, chlorozotocin, fotemustine, lomustine, nimustine, and/or ranimnustine; dynemicin; bisphosphonates-such as clodronate; an esperamicin; a neocarzinostatin chromophore; aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN®. doxorubicin-such as morpholino-doxorubicin, cyanomorpholino-doxorubicin, 2-pyrrolino-doxorubicin and/or deoxydoxorubicin, epirubicin, esorubicin, idarubicin, marcellomycin, mitomycins-such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites-such as methotrexate and 5-fluorouracil (5-FU); folic acid analogues-such as denopterin, methotrexate, pteropterin, trimeterxate; purine analogues-such as fludarabine, 6-mercaptopurine, thiamiprine, thioguanine; pyrimidine analogues-such as ancitabine, azacitidine, 6-azauridine, carmofur, cytarabine, dideoxyuridine, doxifluridine, enocitabine, floxuridine; androgens-such as calusterone, dromostanolone propionate, epitiostanol, mepitiostane, testolactone; anti-adrenals-such as aminoglutethimide, mitotane, trilostane; folic acid replenisher-such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; macrocyclic depsipeptides such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; razoxane; rhizoxin; sizofiran; spirogermanium; tenuazonic acid; triaziquone; 2,2',2"-trichlorotriethylamine; trichothecenes-such as verracurin A, roridin A and/or anguidine; urethan; vindesine; dacarbazine; mannomustine; mitobronitol; mitolactol; pipobroman; gacytosine; arabinoside; cyclophosphamide; thiotepa; taxoids-such as TAXOL®. paclitaxel, abraxane, and/or TAXOTERE®, doxetaxel; chloranbucil; GEMZAR®. gemcitabine; 6-thioguanine; mercaptopurine; methotrexate; platinum analogues-such as cisplatin and carboplatin; vinblastine; platinum; etoposide; ifosfamide; mitoxantrone; vincristine; NAVELBINE®, vinorelbine; novantrone; teniposide; edatrexate; daunomycin; aminopterin; xeloda; ibandronate; topoisomerase inhibitor RFS 2000; difluoromethylomithine (DMFO); retinoids-such as retinoic acid; capecitabine; and pharmaceutically acceptable salts, acids, derivatives or combinations of these.

Examples of tubulin disruptors include taxanes-such as paclitaxel and docetaxel, *vinca* alkaloids, discodermolide, epothilones A and B, desoxyepothilone, cryptophycins, curacin A, combretastatin A-4-phosphate, BMS 247550, BMS 184476, BMS 188791; LEP, RPR 109881A, EPO 906, TXD 258, ZD 6126, vinflunine, LU 103793, dolastatin 10, E7010, T138067 and T900607, colchicine, phenstatin, chalcones, indanocine, T138067, oncocidin, vincristine, vinblastine, vinorelbine, vinflunine, halichondrin B, isohomohalichondrin B, ER-86526, pironetin, spongistatin 1, spiket P, cryptophycin 1, LU103793 (cematodin or cemadotin), rhizoxin, sarcodictyin, eleutherobin, laulilamide, VP-16 and D-24851 and pharmaceutically acceptable salts, acids, derivatives or combinations of these.

Examples of DNA intercalators include acridines, actinomycins, anthracyclines, benzothiopyranoindazoles, pixantrone, crisnatol, brostallicin, CI-958, doxorubicin (adriamycin), actinomycin D, daunorubicin (daunomycin), bleomycin, idarubicin, mitoxantrone, cyclophosphamide, melphalan, mitomycin C, bizelesin, etoposide, mitoxantrone, SN-38, carboplatin, cis-platin, actinomycin D, amsacrine, DACA, pyrazoloacridine, irinotecan and topotecan and pharmaceutically acceptable salts, acids, derivatives or combinations of these.

The drug may be an anti-hormonal agent that acts to regulate or inhibit hormone action on tumours-such as anti-estrogens and selective estrogen receptor modulators, including, but not limited to, tamoxifen, raloxifene, droloxifene, 4-hydroxytamoxifen, trioxifene, keoxifene, LY117018, onapristone, and/or fareston toremifene and pharmaceutically acceptable salts, acids, derivatives or combinations of two or more of any of the above. The drug may be an aromatase inhibitor that inhibits the enzyme aromatase, which regulates estrogen production in the adrenal glands-such as, for example, 4(5)-imidazoles, aminoglutethimide, megestrol acetate, AROMASIN®. exemestane, formestanie, fadrozole, RIVISOR®. vorozole, FEMARA®. letrozole, and ARIMIDEX® and/or anastrozole and pharmaceutically acceptable salts, acids, derivatives or combinations of two or more of any of the above.

Other anti-cancer drugs include anti-androgens-such as flutamide, nilutamide, bicalutamide, leuprolide, goserelin and/or troxacitabine and pharmaceutically acceptable salts, acids, derivatives or combinations of any of these. Alternatively, the anti-cancer drug may be a protein kinase inhibitor, a lipid kinase inhibitor or an anti-angiogenic agent.

In a particular embodiment, the drug is a dolastatin. Dolastatins are antiproliferative agents, inhibiting the growth and reproduction of target cells and inducing apoptosis in a variety of malignant cell types. Two natural dolastatins, dolastatin 10 and dolastatin 15, have been selected for drug development based on their superior antiproliferative bioactivity. The pursuit of synthetic dolastatin analogues has led to the development of LU103793 (cematodin or cemadotin), a dolastatin 15 analogue. ILX-651 is an orally active third generation synthetic dolastatin 15 analogue. In one embodiment, the dolastatin is of the auristatin class. As used herein, the term dolastatin encompasses naturally occurring auristatins and non-naturally occurring derivatives, for example monomethyl auristatin E (MMAE) ((S)—N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido)butanamide) or monomethyl auristatin F (MMAF)((S)-2-((2R,3R)-3-((S)-1-((3R,4S,5S)-4-((S)—N,3-dimethyl-2-((S)-3-methyl-2-(methylamino)butanamido)butanamido)-3-methoxy-5-methylheptanoyl)pyrrolidin-2-yl)-3-methoxy-2-methylpropanamido)-3-phenylpropanoic acid).

Alternatively, the anti-cancer drug may comprise a nucleic acid such as an RNA molecule or nanomolecule which targets an oncogene gene, in particular an RNA molecule such as a small interfering RNA (siRNA), a short hairpin RNA (shRNA), a microRNA (miRNA), or a short activating RNA (saRNA) which are designed to silence or activate genes, and in particular oncogenes. A wide variety of such RNAs are known, and the therapeutic potential of these molecules has been extensively reviewed.[16,17]

The therapeutic agent of the invention comprises a cell binding agent linked to an anti-cancer drug as defined above. The means by which these two entities are linked together will depend upon factors such as the nature of the cell binding agent and the specific nature of the drug. In a particular embodiment, the cell binding agent is linked to the anti-cancer drug by way of a chemical linking group. The chemical linking group is suitably covalently bonded to both the cell binding agent and the anti-cancer drug. It is suitably such that it breaks down in the cell in-vivo to release the anti-cancer drug in a potent form.

Examples of suitable linkers may be chemically-labile, such as acid-cleavable hydrazine linkers or disulphide bonds; enzymatically-labile, such as peptide linkers or carbohydrate moieties; or non-cleavable linkers, such as thioether linkers or amides, as are known in the art.[18]

Generally, a chemical entity comprising the linker group is reacted with the cell binding agent under conditions in which the linker group becomes attached to the cell binding agent, either by conjugation or by covalent bonding.

In a particular embodiment, the chemical entity comprising the linker group is a maleimidocaproyl-valine-citrullin-p-aminobenzyloxycarbonyl linker. This linker is 'self-immolative' in the sense that it breaks down in vivo in a cell to release the anti-cancer drug. The linker exhibits high plasma stability and a protease cleavage site. Enzymatic cleavage leads to 1, 6-elimination of the 4-aminobenzyl group, releasing the anti-cancer drug.[18,19]

The relative amount of drug:cell binding agent may be varied and will depend upon the relative amount of linker applied to the cell binding agent. It should be sufficient to provide a useful therapeutic ratio for the agent, but the loading should not be so high that the structure of the cell binding agent and in particular its ability to enter the cell via the RAGE receptor is compromised. The amounts will therefore vary depending upon the particular cell binding agent and the particular anti-cancer drug used. However, typically the ratio of drug:cell binding agent molecules in the therapeutic agent is in the range of from 1:1 to 1:8, for example from 1:1.5 to 1:3.5.

The therapeutic agents described above are useful in the treatment of gynaecological proliferative disease. In particular, the applicants have found that the cell binding agent will bind to the RAGE receptor of a cell, in particular a gynaecological tumour cell, and become internalised within the cell. At this stage, any chemical linkers may be cleaved or the cell binding agent metabolised allowing the anti-cancer drug or an active metabolite to produce the desired effect. The applicants have found that therapeutic agents of this type are effective against human gynaecological cancer cells as illustrated hereinafter.

The therapeutic agent of the invention is used in the treatment of gynaecological proliferative conditions in which RAGE is overexpressed. The applicants have found that such proliferative conditions include gynaecological cancers such as endometrial or ovarian cancer, as well as endometriosis and polycystic Ovary Syndrome. For example, the agent is used to treat gynaecological cancers as described above, or polycystic Ovary Syndrome For use in these therapies, the therapeutic agents of the invention are suitably administered in the form of a pharmaceutical composition.

Thus a further aspect of the invention provides a pharmaceutical composition comprising a therapeutic agent as described above in combination with a pharmaceutically acceptable carrier.

Suitable pharmaceutical compositions will be in either solid or liquid form. They may be adapted for administration by any convenient peripheral route, such as parenteral, oral, vaginal or topical administration or for administration by inhalation or insufflation. The pharmaceutical acceptable carrier may include diluents or excipients which are physiologically tolerable and compatible with the active ingredient. These include those described for example in Remington's Pharmaceutical Sciences.[20]

Parenteral compositions are prepared for injection, for example subcutaneous, intramuscular, intradermal, and intravenous or via needle-free injection systems. Also, they may be administered by intraperitoneal injection. They may be liquid solutions or suspensions, or they may be in the form of a solid that is suitable for solution in, or suspension in, liquid prior to injection. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like.

Oral formulations will be in the form of solids or liquids, and may be solutions, syrups, suspensions, tablets, pills, capsules, sustained-release formulations, or powders. Oral formulations include such normally employed excipients as, for example, pharmaceutical grades of mannitol, lactose, starch, magnesium stearate, sodium saccharin, cellulose, magnesium carbonate, and the like.

Topical formulations will generally take the form of suppositories, pessaries, intranasal sprays or aerosols, buccal or sublingual tablets or lozenges. For suppositories or pessaries, traditional binders and excipients may include, for example, polyalkylene glycols or triglycerides; such suppositories or pessaries may be formed from mixtures containing the active ingredient. Other topical formulations may take the form of a lotion, solution, cream, ointment or dusting powder that may optionally be in the form of a skin patch.

In a further aspect, the invention provides a method of treating a proliferative disease selected from gynaecological cancer, such as endometrial or ovarian cancer and polycystic ovary syndrome in which RAGE is over expressed, said method comprising administering to a patient in need thereof an effective amount of a therapeutic agent as described above, or a pharmaceutical composition comprising it, also as described above.

The amount of therapeutic agent administered will vary depending upon factors such as the specific nature of the agent used, the size and health of the patient, the nature of the condition being treated etc. in accordance with normal clinical practice. Typically, a dosage in the range of from 0.01-1000 mg/Kg, for instance from 0.1-10 mg/Kg, would produce a suitable therapeutic or protective effect.

Dosages may be given in a single dose regimen, split dose regimens and/or in multiple dose regimens lasting over several days. Effective daily doses will, however vary depending upon the inherent activity of the therapeutic agent, such variations being within the skill and judgment of the physician.

The therapeutic agent of the present invention may be used in combination with one or more other active agents, such as one or more pharmaceutically active agents. In particular, the applicants have found that anti-hormonal agents such as anti-estrogens and/or selective estrogen receptor modulators such as tamoxifen, may themselves upregulate RAGE expression in gynaecological cancer. Therefore, these agents may act synergistically with the agents of the invention, when the anti-cancer drug carried by the ADC may be the same or different.

Therapeutic agents of the invention may be prepared using conventional methods.

In particular they may be produced by linking together a cell binding agent which binds the RAGE and an anti-cancer drug.

Suitable methods comprise reacting a moiety comprising the linking group with one of either an anti-cancer drug or a cell binding agent, and contacting the product with the other of the anti-cancer drug and the cell binding agent to form the therapeutic agent.

In particular, where the anti-cancer drug is a small molecule, the linking group may be incorporated during the manufacturing process. Thus a particular cytotoxin with a linker attached is Maleimidocaproyl-Val-Cit-PABC-MMAE of structure (I)

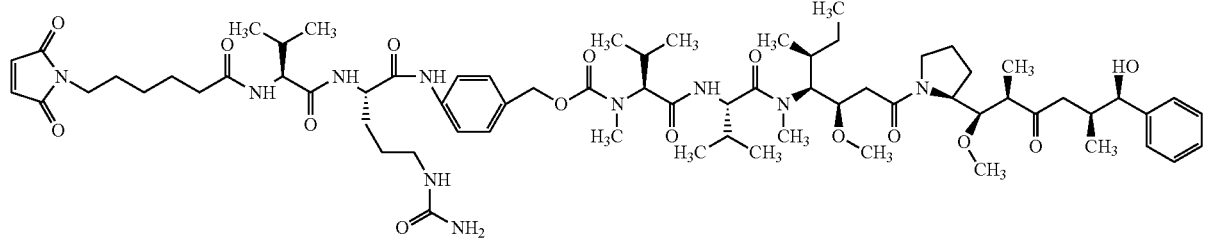

(I)

This structure includes the self-immolative linker group maleimidocaproyl-valine-citrulline-p-aminobenzyloxy carbonyl.

Thus in a particular embodiment, in a first step, a linking group is added to the anti-cancer drug and one or more of the resulting product is reacted with the cell binding agent. Suitable reaction conditions for the manufacture of linker attached cytotoxic agents could comprise those described by Doronina et al 2006.[19] Suitable reaction conditions for the attachment of linker attached cytotoxic agents such as maleimidocaproyl-Val-Cit-PABC-MMAE, could also comprise those described by Doronina et al 2006.[19] Specific conditions for each of the stages would be understood or could be determined by the skilled person.

BRIEF DESCRIPTION OF THE SEVERAL VIEWS OF THE DRAWINGS

The invention will now be particularly described by way of example with reference to the accompanying diagrammatic drawings in which

FIG. 20 is a series of graphs showing cell survival data for a range of cell lines when treated with ADCs in accordance with the invention;

DETAILED DESCRIPTION OF THE INVENTION

EXAMPLE 1

Figure 1:
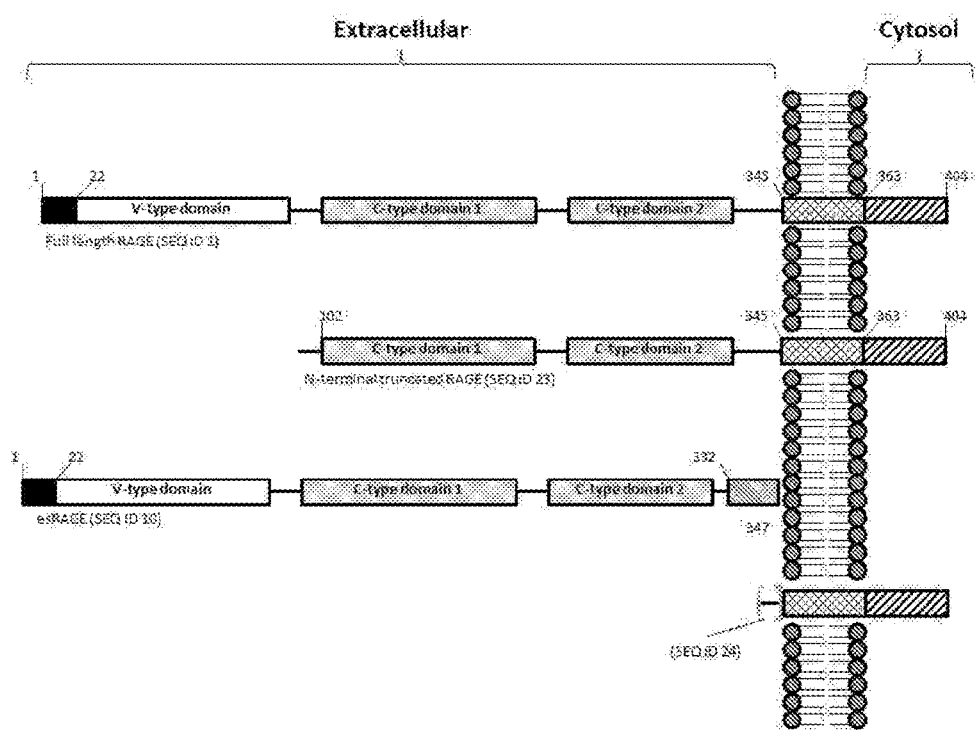
FIG. 1 is a graphical representation of the multiligand transmembrane receptor of the immunoglobulin superfamily, RAGE and some of its variant forms.
Figure 2:
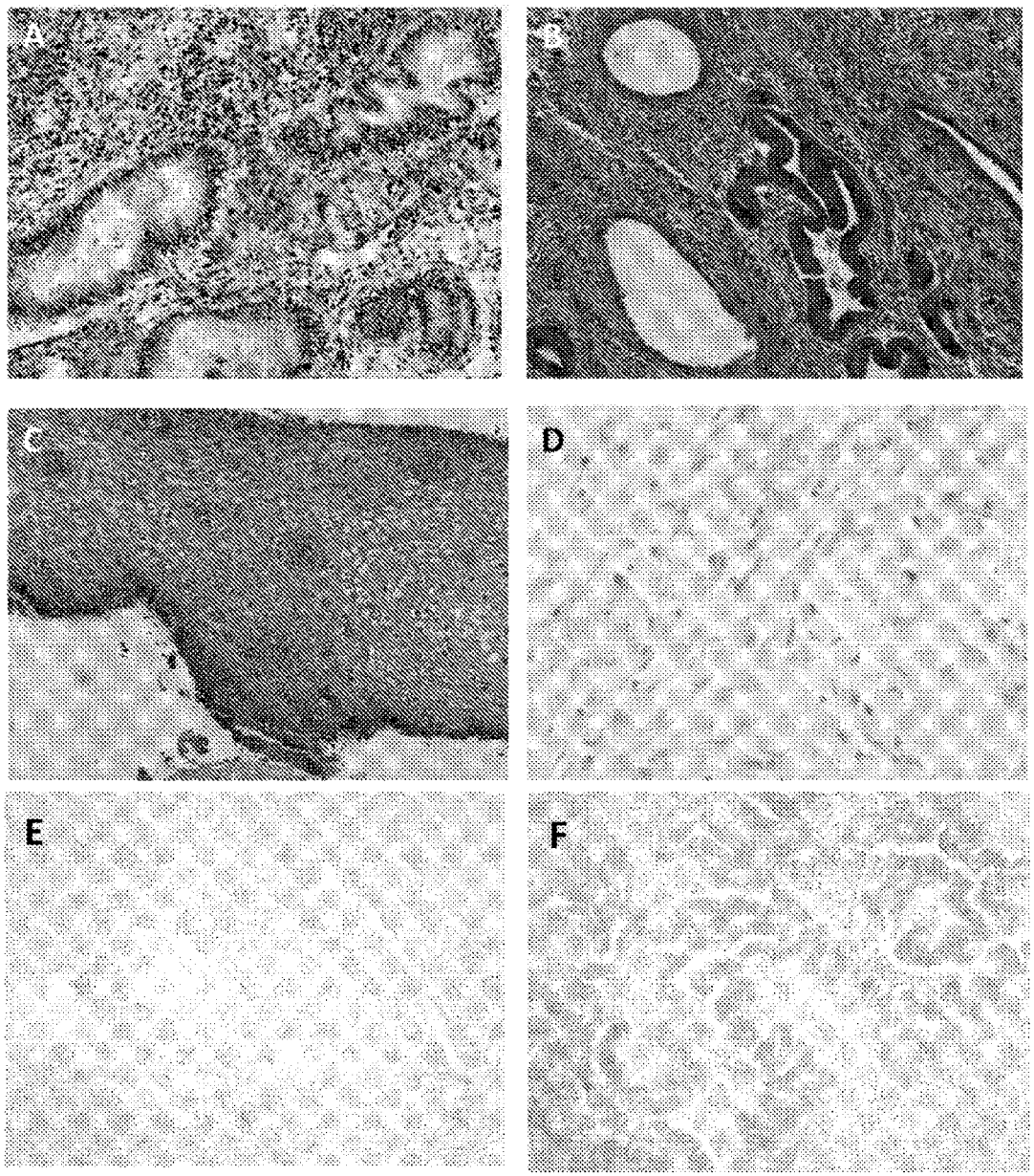
FIG. 2 is a series of images showing RAGE protein expression in biopsies from the endometrium and ovary of a healthy patient and patients with endometrial or ovarian cancer.

Expression of RAGE in Gynaecological Cancers and Non Oncological Proliferative Conditions Endometrial biopsies were collected from the endometrium of a healthy patient (FIG. 2A), and patients with endometrial cancer (FIG. 2B), endometrial hyperplasia (FIG. 2C), or endometriosis (FIG. 2D). Biopsies were fixed and paraffin embedded for analysis of RAGE expression by immunohistochemistry.

Further biopsy images show RAGE expression in a healthy ovary (FIG. 2E) and ovarian cancer (endometrioid adenocarcinoma; FIG. 2F). Positive staining was observed in the epithelial cells of the ovarian cystic masses whereas healthy tissue did not express the target.

The expression of AGER mRNA in four endometrial epithelial cell lines derived from two well-differentiated type I and type II adenocarcinomas; HEC1 (HEC1A, HEC1B, HEC50) and Ishikawa respectively, was measured. Epithelial cells were cultured in 6-well plates in control medium. Total RNA was extracted once cells reached confluence for analysis of AGER mRNA expression by quantitative PCR. Data are presented as box plots showing the median (line), $25^{th}$ and $75^{th}$ percentiles (box) and $10^{th}$ and $90^{th}$ percentile (whiskers), n=5, in FIG. 3A.

In a further experiment, RAGE protein expression was measured in the endometrial biopsies from patients diagnosed with hyperplasia, endometrial cancer Type I or Type II and postmenopausal (PM) controls by immunohistochemistry. Endometrial biopsy samples were grouped as follows: PM (n=25, median=0.2), Hyperplasia (n=21, median=5.5), type I EC (n=18, median=1.5), type II EC (n=17, median=2). IHC samples were scored blind by three independent observers. Values shown are median IHC scores and statistical analysis was performed using a Mann-Whitney test *p<0.05, **p<0.01, compared to PM control.

Figure 3:
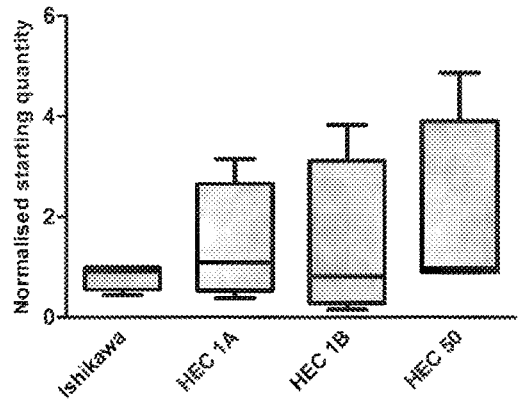
FIG. 3 is a series of graphs showing (A) the expression of AGER mRNA in four endometrial epithelial cell lines derived from two well-differentiated type I and type II adenocarcinomas; HEC1 (HEC1A, HEC1B, HEC50) and Ishikawa respectively; (B) the results of an immunohistochemistry study showing that endometrial RAGE is overexpressed in hyperplasia and Endometrial cancer; and (C) immunohistochemistry results for RAGE staining in healthy ovary or ovarian cancer (OC) biopsies.
Figure 3:
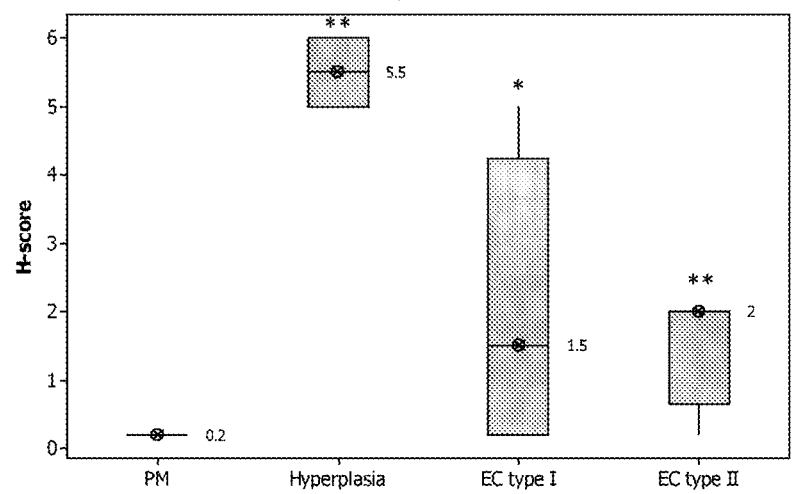
Figure 3:
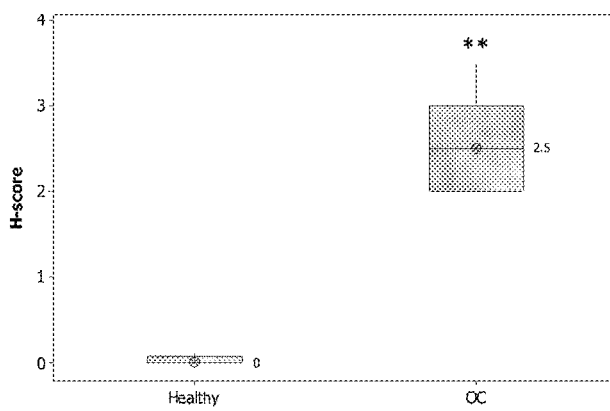

The results are shown in FIG. 3B. RAGE expression was noted in the membrane and cytoplasm of the tumour cells as well as endometrial cells obtained from hyperplasia patients. PM staining was almost negative. Statistically significant differences in RAGE expression were observed between PM control and all study groups.

RAGE protein expression was also measured by Immunohistochemistry in ovarian biopsies from patients diagnosed with ovarian cancer (n=19) and healthy control patients (n=8). IHC samples were scored blind by three independent observers. The results are shown graphically in FIG. 3C. Values shown are median IHC scores and statistical analysis was performed using a Mann-Whitney test, **p<0.01, compared to healthy control.

Figure 4:
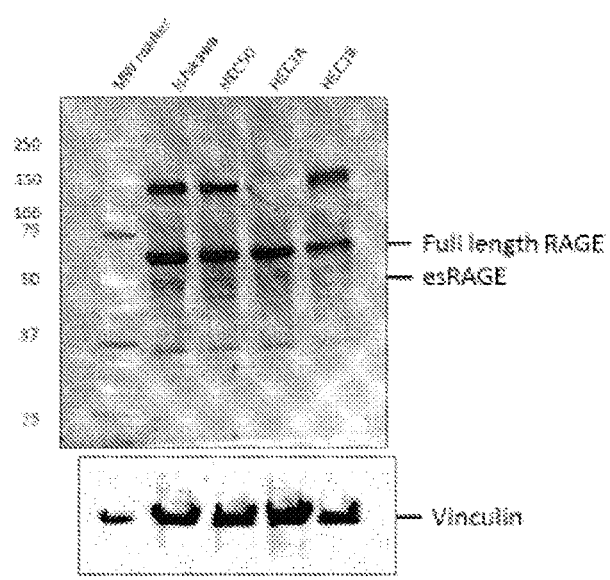
FIG. 4 is a series of Western blots showing RAGE protein expression in the cell lines of FIG. 3.
Figure 5:
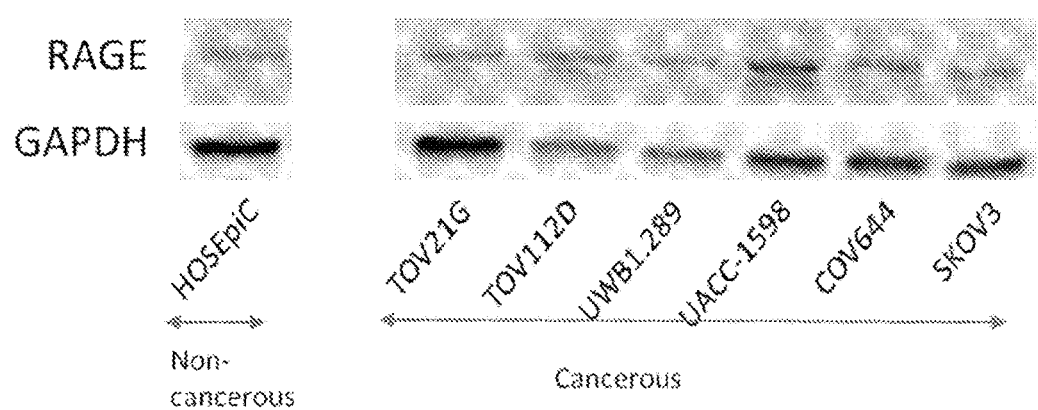
FIG. 5 is representative Western blots showing expression of RAGE protein in six ovarian cancer cell lines: TOV21G, TOV112D, UWB1.289, UACC-1598, COV644 and SKOV3, and one normal ovarian cell line: HOSEpiC.

RAGE protein expression in the four endometrial cancer epithelial cell lines (HEC1A, HEC1B, HEC50 and Ishikawa), six ovarian cancer epithelial cell lines (TOV21G, TOV112D, UWB1.289, UACC-1598, COV644, SKOV3) and a non-cancerous ovarian cell line (HOSEpiC) were determined by Western blot. Epithelial cells were cultured in 6-well plates in control medium. Protein was extracted once cells reached confluence for analysis of RAGE protein expression. Data are presented as representative Western blots for endometrial and ovarian cell lines, FIGS. 4 and 5, respectively.

These results clearly show that RAGE is upregulated in these gynaecological cancers.

Figure 6:
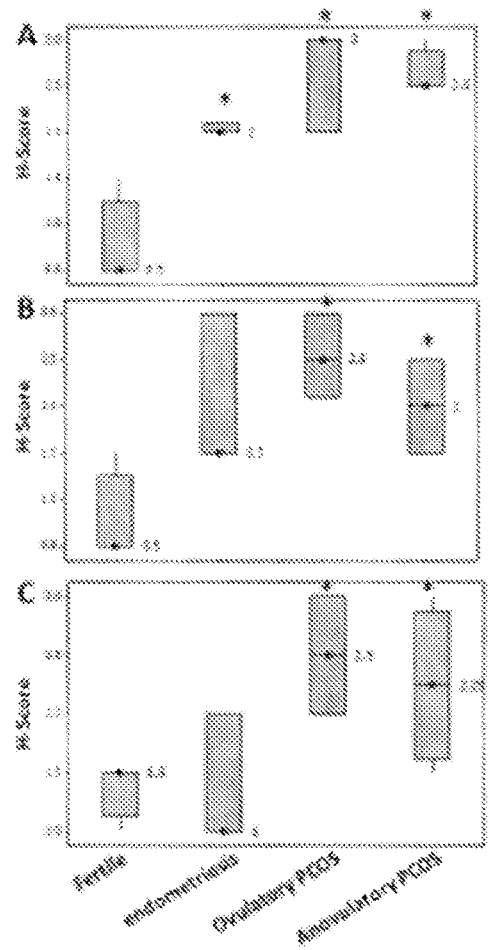
FIG. 6 is a series of graphs showing RAGE expression scoring (intensity and distribution: H-score) in endometrial biopsy samples, taken during the proliferative phase of the menstrual.

In further experiments, endometrial biopsies were collected from patients during the proliferative phase (n=32) of the menstrual cycle, and subdivided into four groups: fertile (n=9), endometriosis (n=11), ovulatory PCOS (n=12) or anovulatory PCOS (n=14). Biopsies were fixed and paraffin embedded for analysis of RAGE expression by immunohistochemistry. RAGE expression scoring (intensity and distribution: H-score) in glandular epithelium (A), luminal epithelium (B) and stroma (C) was performed blind, by three independent reviewers. The results are shown in FIG. 6. Data are presented as box plots showing the median (line), $25^{th}$ and $75^{th}$ percentiles (box) and $10^{th}$ and $90^{th}$ percentile (whiskers), and analysed by Mann-Whitney U test, values differ from fertile: * P<0.05.

In a separate test, endometrial biopsies were collected from patients during the secretory phase (n=41) of the menstrual cycle, and, as before, subdivided into four groups: fertile (n=12), endometriosis (n=18), ovulatory PCOS (n=11) or anovulatory PCOS (n=14). Biopsies were fixed and paraffin embedded for analysis of RAGE expression by immunohistochemistry.

Figure 7:
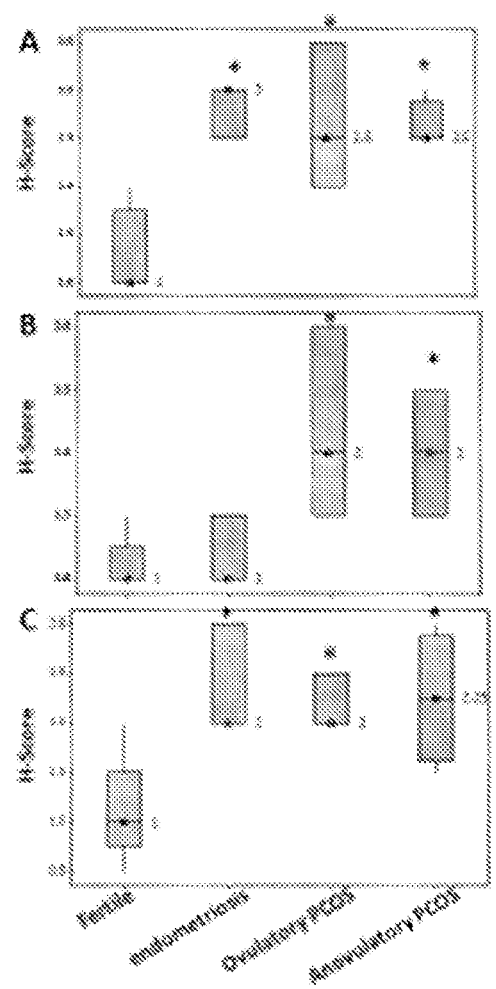
FIG. 7 is a series of graphs showing RAGE expression scoring (intensity and distribution: H-score) in endometrial biopsy samples, taken during the secretory phase of the menstrual cycle.

RAGE expression scoring (intensity and distribution: H-score) in glandular epithelium (A), luminal epithelium (B) and stroma (C) was performed blind, by three independent reviewers. The results are shown in FIG. 7. Data are presented as box plots showing the median (line), $25^{th}$ and $75^{th}$ percentiles (box) and $10^{th}$ and $90^{th}$ percentile (whiskers), and analysed by Mann-Whitney U test, values differ from fertile: * P<0.05.

Figure 8:
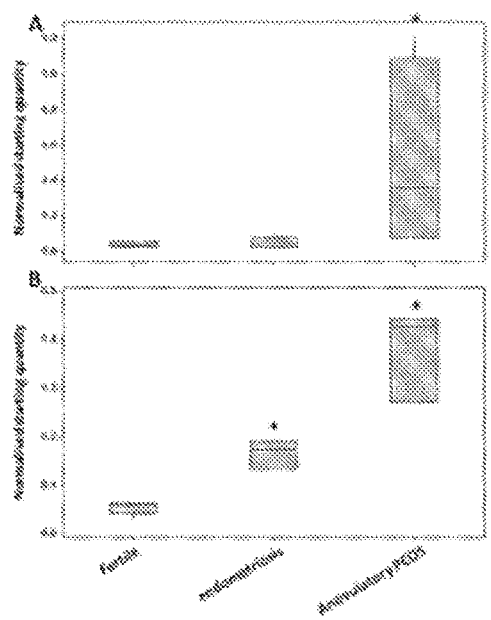
FIG. 8 is a series of graphs showing AGER mRNA expression in endometrial biopsy samples taken from polycystic ovary syndrome patients during the proliferative phase of the menstrual cycle.
Figure 9:
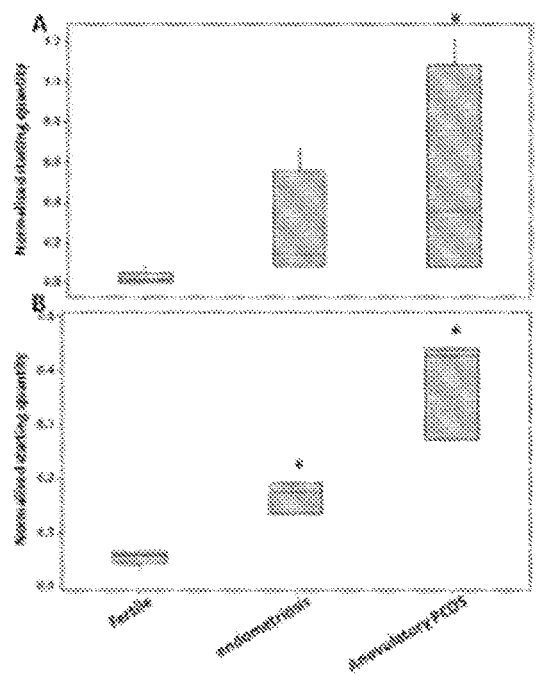
FIG. 9 is a series of graphs showing AGER mRNA expression in endometrial biopsy samples taken from polycystic ovary syndrome patients, during the secretory phase of the menstrual cycle.

In another set of experiments, endometrial biopsies were collected from patients suffering from polycystic ovary syndrome during the proliferative phase and secretive phase (n=32) of the menstrual cycle, and subdivided into three groups: fertile (n=2), endometriosis (n=6) or anovulatory PCOS (n=7). Total RNA was extracted from whole endometrial biopsies (A) and endometrial epithelial biopsies (B) for analysis of AGER mRNA expression by quantitative PCR. The results are shown in FIGS. 8 and 9, respectively. Data are presented as box plots showing the median (line), $25^{th}$ and $75^{th}$ percentiles (box) and $10^{th}$ and $90^{th}$ percentile (whiskers), and analysed by Mann-Whitney U test, values differ from fertile: * P<0.05.

These data show that expression of AGER mRNA and its protein product RAGE is increased in endometrial and ovarian cancers, as well as endometriosis, hyperplasia and polycystic ovary syndrome patients during the proliferative and secretive phase of the menstrual cycle. AGER mRNA expression is also increased in endometrial epithelial cells during the proliferative and secretive phases of the menstrual cycle, and RAGE protein expression is increased in endometrial epithelium during the proliferative phase, and in the endometrial epithelium and stroma during the secretive phase of the menstrual cycle.

EXAMPLE 2

Efficacy of RAGE as a Carrier

Figure 10:
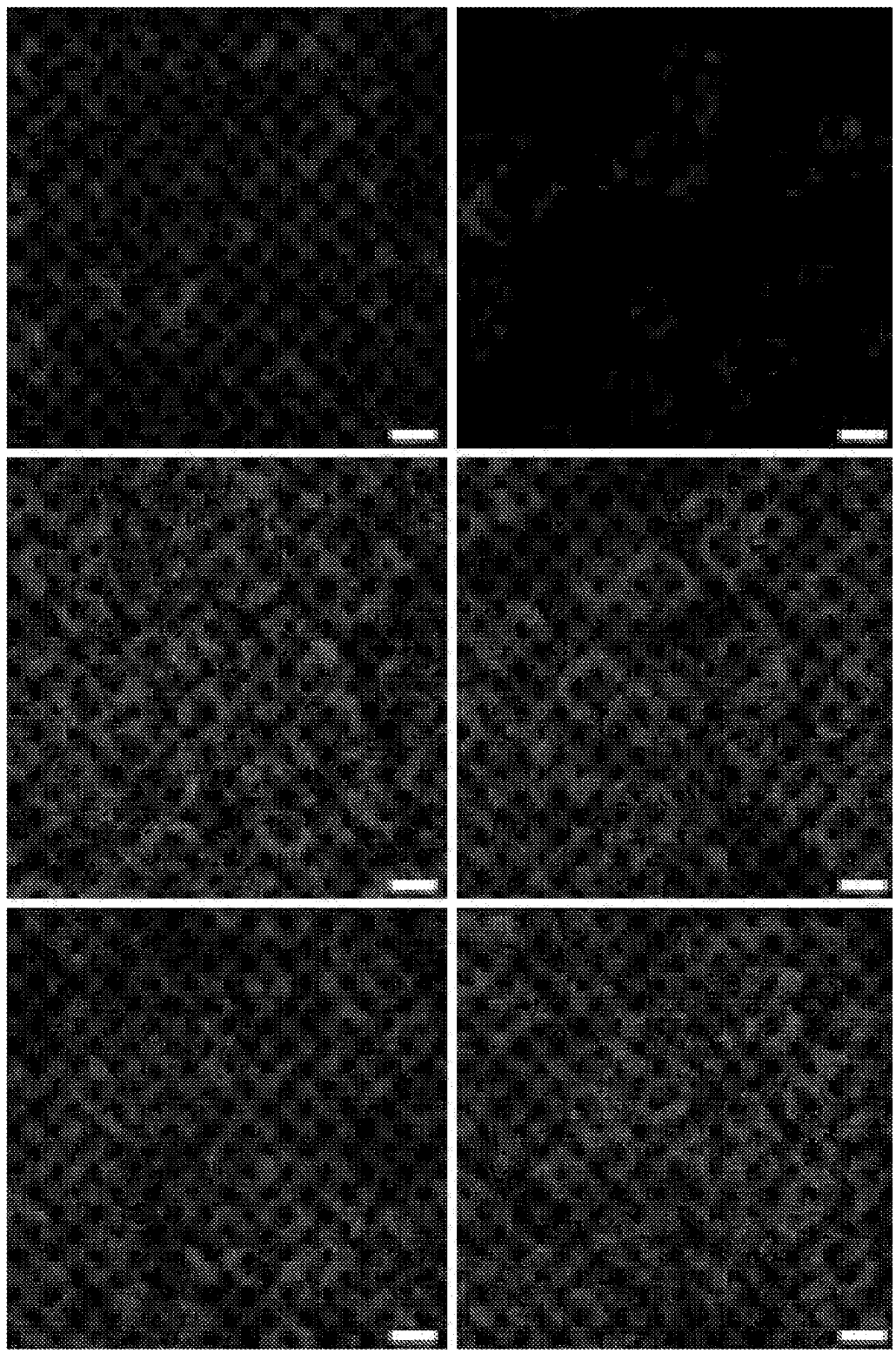
FIG. 10 is a series of confocal microscopy images showing the internalisation of anti-RAGE antibody in HEC 1A cells.

HEC 1A cells derived from an endometrial adenocarcinoma were cultured on 8-well chamber slides to 80% confluence. Cells were treated with murine, anti-human RAGE (MAB11451; Clone 176902) for the times shown. Cells were fixed and permeabalised, before staining with anti-murine FITC-labelled secondary antibody. Representative images were acquired on a Zeiss 710 confocal microscope and examples are shown in FIG. 10.

This showed that Anti-RAGE antibody is rapidly internalised in cells, making it a good carrier for drugs.

EXAMPLE 3

Preparation of Antibody-drug Conjugates

A murine IgG2B antibody against recombinant human RAGE (R&D Systems Cat No. MAB11451) was reconstituted to 1.59 mg/mL in 10 mM Tris/Cl, 2 mM EDTA pH 8.0. The antibody was reduced with 3.5 molar equivalents of 10 mM TCEP:Ab in water for 2 h at 37° C. Without purification the reduced antibody was split in two one each half alkylated with 6.5 molar equivalents of 10 mM vcMMAE or mcM-MAF:Ab in DMA (final DMA concentration in the alkylation mixture was 5% v/v) for 2 h at 22° C. Following alkyation N-acetyl cysteine was used to quench any unreacted toxin linker. The conjugates were purified using a HiTrap G25 column equilibrated in 5 mM histidine/Cl, 50 mM trehalose, 0.01% w/v olysorbate 20, pH 6.0. The conjugates were analysed by size exclusion chromatography for monomeric content and concentration (using a calibration curve of naked antibody) using size exclusion chromatography. Running conditions: Agilent 1100 HPLC, TOSOH TSKgel G3000SWXL 7.8 mm×30 cm, 5 μm column, 0.5 mL/min in, 0.2 M Potassium Phosphate, 0.25 M Potassium Chloride, 10% IPA, pH 6.95. Drug loading of the conjugates was confirmed using a combination of HIC and reverse phase chromatography. HIC was carried out using a TOSOH Butyl-NPR 4.6 mm×3.5 cm, 2.5 μm column run at 0.8 mL/min with a 12 min linear gradient between A—1.5M (NH4)2SO4, 25 mM NaPi, pH 6.95±0.05 and B—75% 25 mM NaPi, pH 6.95±0.05, 25% IPA. Reverse phase analysis was performed on a Polymer Labs PLRP 2.1 mm×5 cm, 5 μm column run at 1 mL/min at 80° C. with a 25 min linear gradient between 0.05% TFA/H2O and 0.04% TFA/CH3CN. Samples were first reduced by incubation with DTT at pH 8.0 at 37° C. for 15 min. Due to the complex disulphide structure of an IgG2B and hence potential conjugation site variability both the HIC and PLRP chromatographic patterns were too complex to provide an accurate estimation of average drug loading but did confirm a significant level of drug conjugation.

The resulting RAGE ADC was designated 'SNIPER'.

EXAMPLE 4

Effects of ADC on Human Gynaecological Cancer Cells

The cytotoxicity of the SNIPER ADC prepared in Example 3 was tested in a direct comparison to treatment with drug alone or anti-RAGE antibody alone.

Figure 11:
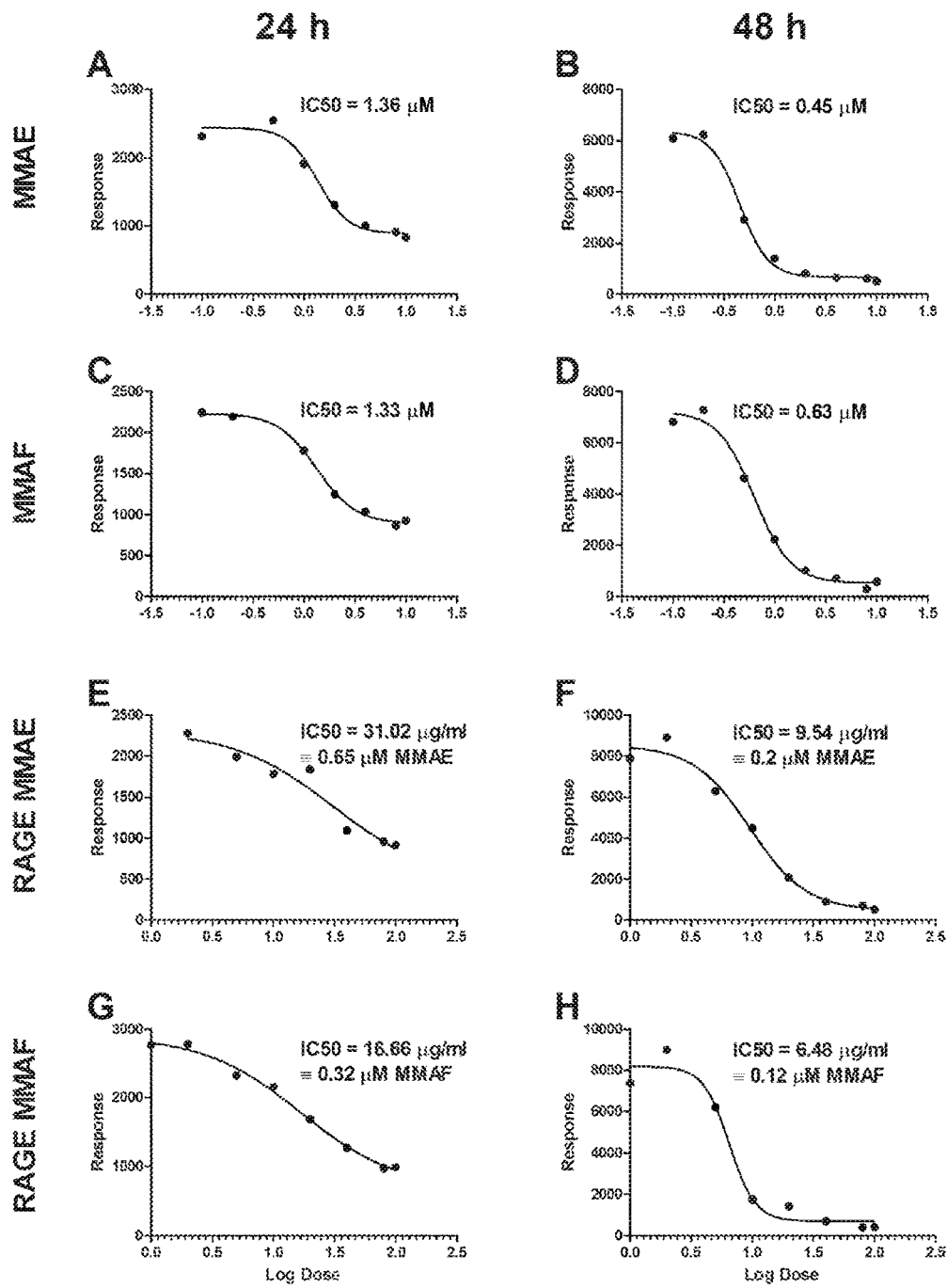
FIG. 11 is a series of graphs illustrating how delivering cytotoxins in the form of RAGE targeting ADC improves drug potency in endometrial cancer cells.

Endometrial (Ishikawa) or ovarian (TOV112D) cancer cells were cultured in 96-well plates and treated with an extended concentration range of MMAE, MMAF, RAGE MMAE or RAGE MMAF for 24 or 48 h. Data was analysed by non-linear regression and IC50 concentrations determined for each treatment. After 24 h treatment, RAGE MMAE (FIG. 11E: IC50=31.02 μg/ml≡0.65 as MMAE μM MMAE) was twice as potent as MMAE alone (FIG. 11A: IC50=1.4 μM), whilst RAGE MMAF (FIG. 11G: IC50=16.66 μg/ml≡0.32 μM MMAF) was four times more potent as MMAF alone (FIG. 11C: IC50=1.3 μM). After 48 h treatment, RAGE MMAE (FIG. 11F: IC50=9.54 μg/ml≡0.2 as MMAE μM MMAE) was again twice as potent as MMAE alone (FIG. 11B: IC50=0.46 μM), and RAGE MMAF (FIG. 11H: IC50=6.48 μg/ml≡0.12 μM MMAF) was five times more potent as MMAF alone (FIG. 11D: IC50=0.63 μM).

Figure 12:
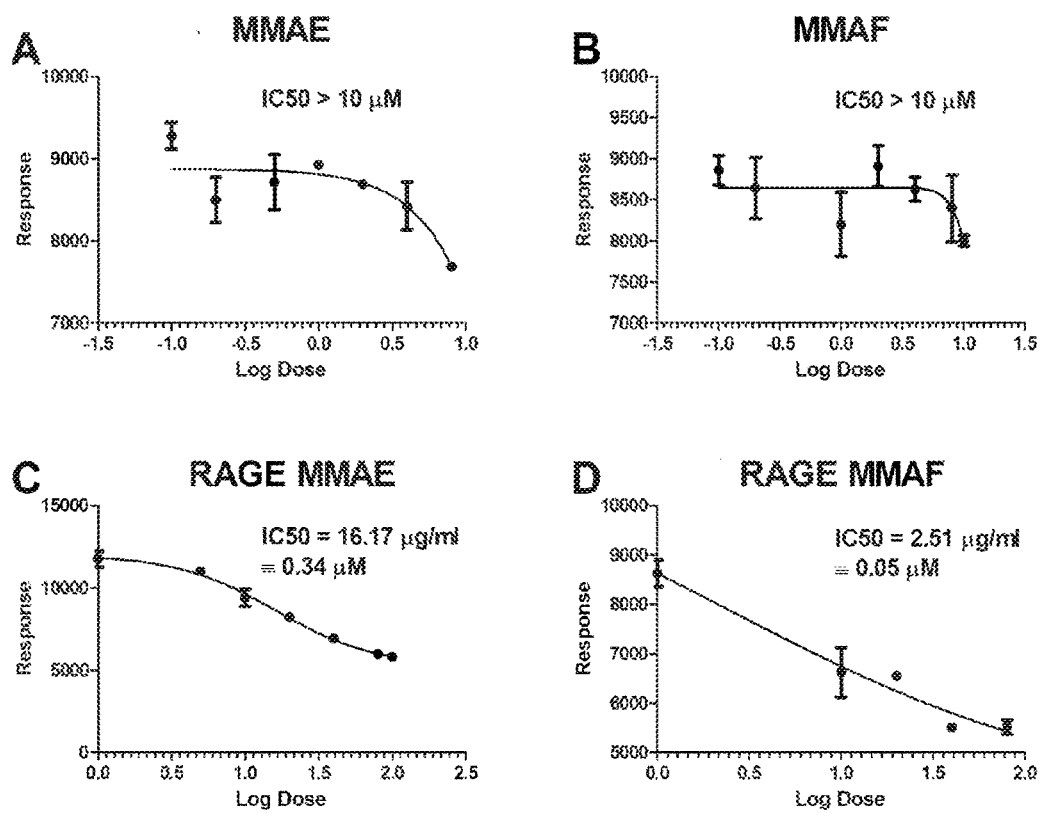
FIG. 12 is a series of graphs showing how delivering cytotoxins in the form of RAGE targeting ADC improves drug potency in ovarian cancer cells.

IC50 concentrations in ovarian (TOV112D) cancer cells after 24 h treatment were 16.67 µg/ml (≡0.65 µM MMAE) for RAGE MMAE (FIG. 12C) and 2.5 µg/ml (≡0.05 µM MMAF) for RAGE MMAF (FIG. 12D). It was not possible to determine IC50 values for the MMAE or MMAF treatments (FIGS. 12A & B, respectively) alone in these cells (i.e. the IC50 was greater than the top concentration tested).

These data demonstrate that delivering cytotoxic agents in the form of a RAGE targeting ADC increases the potency of the drug.

Figure 13:
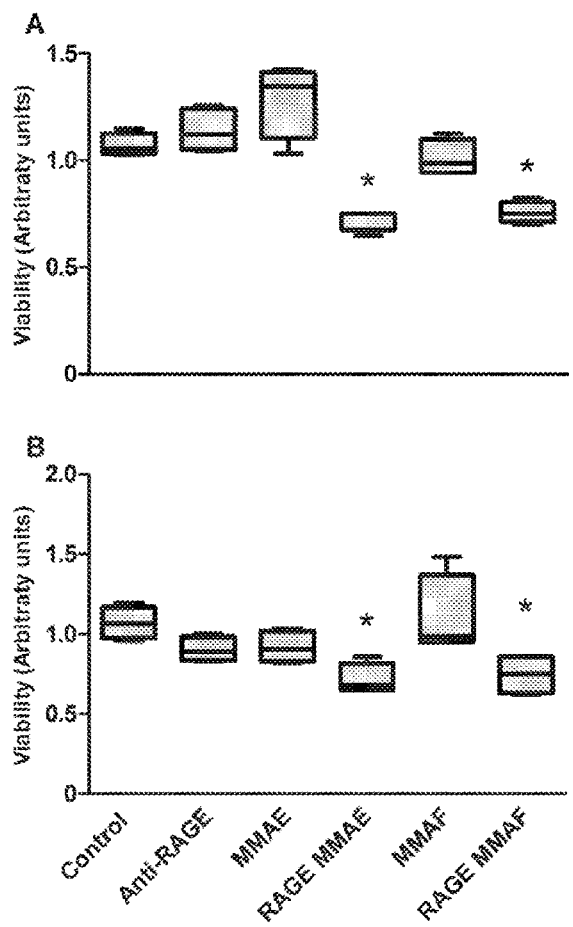
FIG. 13 is a series of graphs showing that RAGE targeting ADCs are more potent killers of endometrial cancer cells than cytotoxin or antibody treatment alone.
Figure 14:
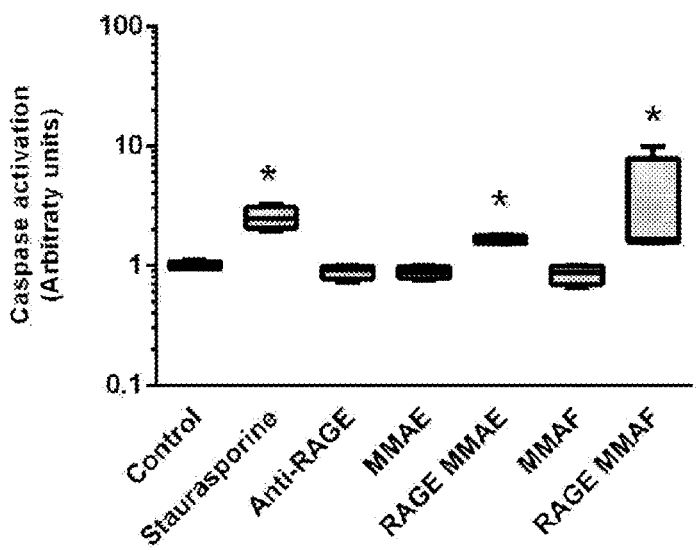
FIG. 14 is a graph illustrating that RAGE targeting ADCs induce apoptosis of endometrial cancer cells.

In separate experiments, Ishikawa (A) or HEC1A (B) cells were seeded into 96-well plates and treated with control medium or medium containing MMAE, MMAF, anti-RAGE antibody, SNIPER MMAE or SNIPER MMAF (shown as RAGE MMAE and RAGE MMAF respectively in FIG. 13) for 24 h. After treatment, cell viability in both cell lines (FIG. 13), and cell apoptosis in Ishikawa cells (caspase activation; FIG. 14) were determined by a fluorescence-based cell viability assay (Apotox Glo Triplex assay, Promega) according to the manufacturer's instructions. Data are presented as box plots showing the median (line), $25^{th}$ and $75^{th}$ percentiles (box) and $10^{th}$ and $90^{th}$ percentile (whiskers), n=4. Data were analysed by ANOVA and Dunnett's pairwise multiple comparison t-test. Values differ from control: * $P<0.05$. Cell killing and the induction of apoptosis was significantly increased following treatment with ADCs compared to treatment with the drug or antibody alone.

Figure 15:
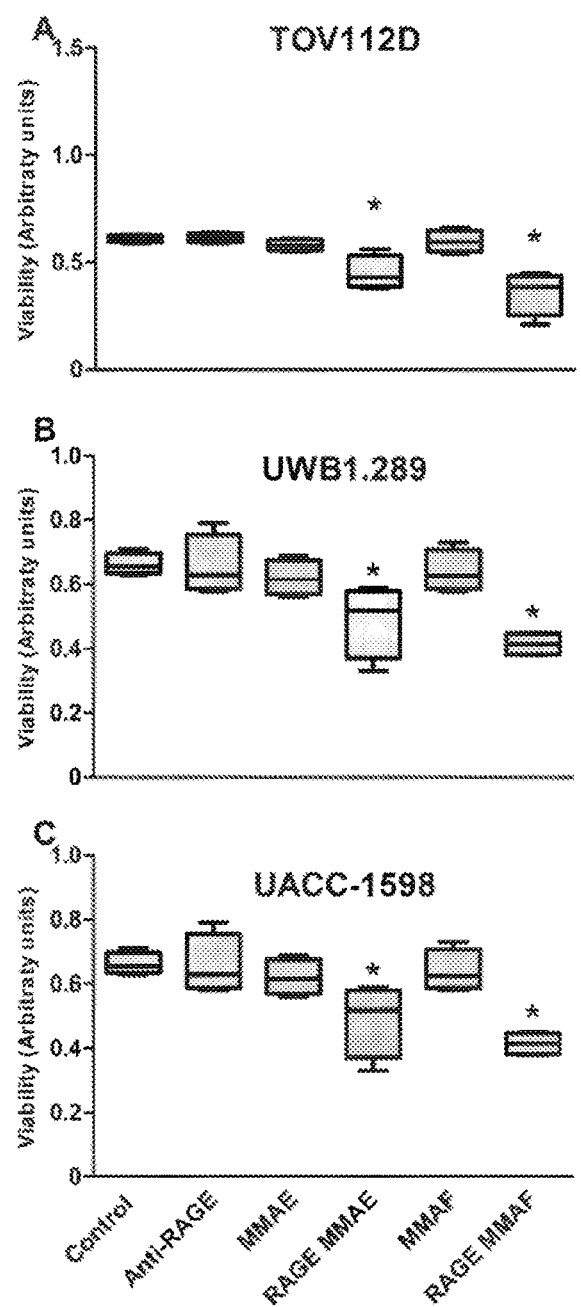
FIG. 15 is a series of graphs showing that RAGE targeting ADCs are more potent killers of ovarian cancer cells than cytotoxin or antibody treatment alone.
Figure 16:
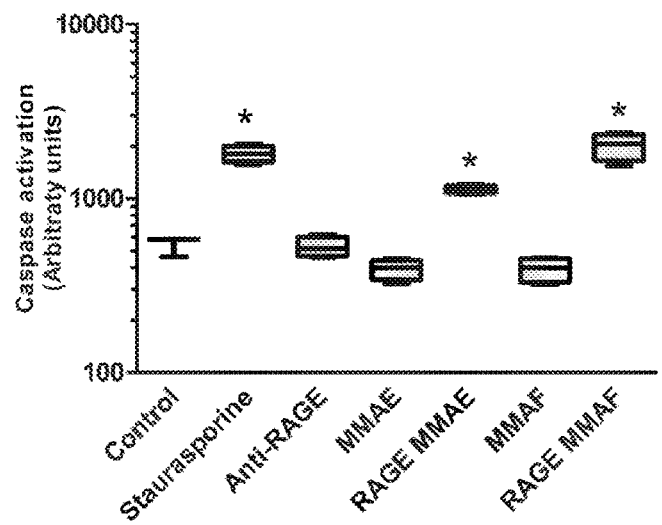
FIG. 16 is a graph showing that RAGE targeting ADCs induce apoptosis of ovarian cancer cells.

In separate experiments, TOV112D, UWB1.289 or UACC-1595 cells were seeded into 96-well plates and treated with control medium or medium containing MMAE, MMAF, anti-RAGE antibody, SNIPER MMAE or SNIPER MMAF for 24 h. After treatment, cell viability in TOV112D, UWB1.289 and UACC-1595 cells (FIG. 15) and the degree of apoptosis in TOV112D cells (caspase activation; FIG. 16) were determined by a fluorescence-based cell viability assay (Apotox Glo Triplex assay, Promega) according to the manufacturer's instructions. Data are presented as box plots showing the median (line), $25^{th}$ and $75^{th}$ percentiles (box) and $10^{th}$ and $90^{th}$ percentile (whiskers), n=4. Data were analysed by ANOVA and Dunnett's pairwise multiple comparison t-test. Values differ from control: * $P<0.05$. Cell killing and the induction of apoptosis was significantly increased following treatment with ADCs compared to treatment with the drug or antibody alone.

These data demonstrate that treating cancerous cells with ADCs targeting RAGE is an effective killing strategy that significantly improves the efficacy of the conjugated cytotoxin.

EXAMPLE 5

Comparison of Cleavable and Non-cleavable Linkers

Figure 17:
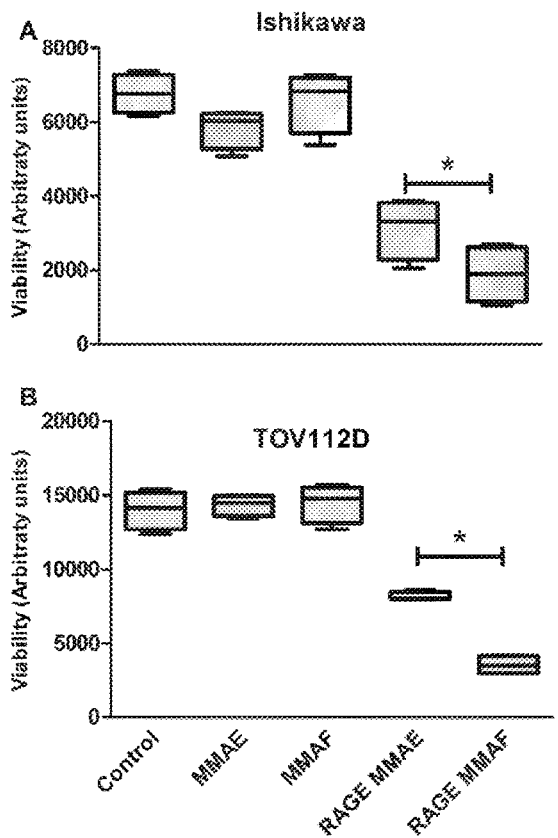
FIG. 17 is a graph illustrating how using a non-cleavable linker improves ADC potency in endometrial (Ishikawa) and ovarian (TOV112D) cancer cells.

The linkers used in Examples 3 & 4 were directly compared. Ishikawa or TOV112D cells were seeded into 96-well plates and treated with control medium or medium containing MMAE, MMAF, SNIPER MMAE or SNIPER MMAF for 24 h. After treatment, cell viability (FIG. 17) was determined by a fluorescence-based cell viability assay (Apotox Glo Triplex assay, Promega) according to the manufacturer's instructions. Data are presented as box plots showing the median (line), $25^{th}$ and $75^{th}$ percentiles (box) and $10^{th}$ and $90^{th}$ percentile (whiskers), n=4. Data were analysed by ANOVA and Dunnett's pairwise multiple comparison t-test. Values differ between groups: * $P<0.05$. SNIPER ADCs were used at 20 µg/ml and drug alone treatments were at equivalent molar concentrations. Cell killing was increased following treatment with ADCs comprising the non-cleavable linker, MMAF, compared to the cleavable linker, MMAE.

These data demonstrate the importance of the correct antibody-linker-drug combination for effective cancer cell killing.

EXAMPLE 6

Internalisation of Anti-RAGE Antibodies in Ovarian and Endometrial Cells

Using conventional methods as described for example in Köhler, G. & Milstein, C. *Nature* 256, 495-497 (1975 and Köhler, G. & Milstein, C. *Eur. J. Immun.* 6, 511-519 (1976), a series of anti-RAGE antibodies were developed. These were designated AA4, HG6 and DF6. The VH protein sequence of AA4 was as shown in SEQ ID NO 25 and the VL protein sequence of AA4 was as shown in SEQ ID NO 26. The VH protein sequence of HG6 was as shown in SEQ ID NO 25 and the VL protein sequence of HG6 was as shown in SEQ ID NO 26. The VH protein sequence of DF6 was as shown in SEQ ID NO 25 and the VL protein sequence of DF6 was as shown in SEQ ID NO 26.

Figure 18:
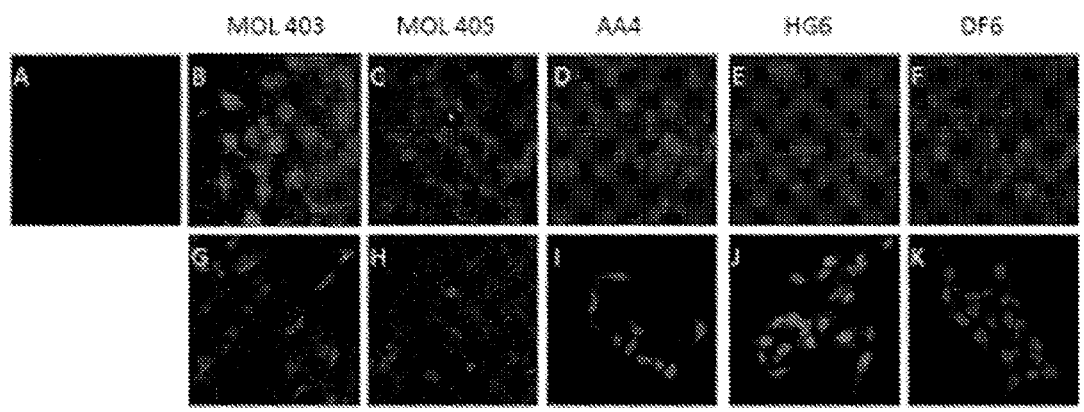
FIG. 18 is a series of confocal microscopy images showing antibody internalisation in ovarian (B-F) and endometrial cancer cells (G-K) that have been treated with 5 different anti-RAGE antibodies.

TOV112D ovarian (B-F) or HEC 1A endometrial (G-K) cancer cells were cultured on 8-well chamber slides to 80% confluence. Cells were treated with different anti-human RAGE antibodies for 1 h. The antibodies used were MOL403, MOL405, AA4, HG6 and DF6, which bind to the following regions of RAGE, respectively: V-type domain, stub region (SEQ ID No. 24), C-type domain 1, C-type domain 1 and stub region (SEQ ID No. 24). Cells were fixed and permeabilised, before staining with FITC or Alexfluor 488 labelled secondary antibody. Representative images were acquired on a Zeiss 710 confocal microscope and the results are shown in FIG. 18.

All antibodies were internalised in the cells, but internalisation of the MOL403 (V-type domain binding) antibody was assessed as being significantly greater than the other antibodies tested.

EXAMPLE 7

Effects of ADC on Healthy and Cancer Cells Over 96 Hours

The methodology of Example 4 was repeated over a 96 h period, using a range of cell lines including endometrial cancer cell lines, Ishikawa, HEC1A, HEC1B, HEC50 and ovarian cancer cells TOV112D as well as healthy endometrial and ovarian cells. The antibody construct used was the SNIPER construct of Example 3.

Results are shown in Table 1 hereinafter. The results show that ADCs are more efficacious after 96 h. In addition, it is clear from Table 1 that the SNIPER-ADC kills endometrial/ovarian cancer cells more effectively than the healthy control cells.

EXAMPLE 8

Relative Efficacy of RAGE ADCs Against Gynaecological Cancer Cells

Figure 19:
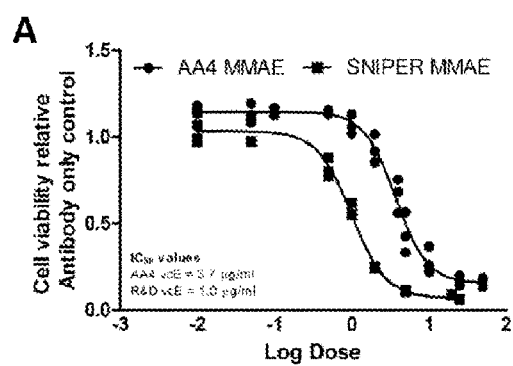
FIG. 19 is a series of graphs showing cell survival rates in HEC 1A cells when treated with ADCs in accordance with the invention. (A) IC50 curves at 96 h, and (B) a time-course graph of cells treated with ADCs (5 μg/ml)

Analysis of the cell killing abilities of ADCs comprising the antibody clones AA4, HG6 and DF6 with MMAE or MMAF, revealed that they were less efficacious than the SNIPER ADC. Antibodies were conjugated to MMAE or MMAF as previously described, and cell viability over a period of 24 to 96 h was determined, also as previously described. Within the concentration ranges tested, 0.01 to 100 µg/ml; it was not possible to determine IC50 values for any of the new antibody clones at the 24, 48 or 72 h time points. After 96 h exposure, IC50 values were determined, showing that the ADCs were less efficacious than the SNIPER ADC at 96 h. An example IC50 comparison graph is shown in FIG. 19A. In addition, comparison of cell killing during the course of the experiment demonstrated that the SNIPER ADC was significantly more effective than the other ADCs (a comparison between AA4 MMAE and SNIPER MMAE is shown in FIG. 19B).

Comparisons of the AA4, HG6 and DF6 ADCs to the SNIPER ADC were made within normal ovarian (HOSEpic) and ovarian cancer (TOV112D and SKOV3) cells, and normal endometrial (Healthy) and endometrial cancer (HEC1A, HEC1B and Ishikawa) cells. Cells were treated for 96 h with 5 μg/ml of each of the ADCs, and cell health monitored as previously described. Within the ovarian cell lines, the SNIPER MMAE ADC was more efficacious compared to the other MMAE ADCs in SKOV3 cells, whilst the SNIPER MMAF ADC was more efficacious in TOV112D and SKOV3 cells (FIG. 20A, B). Data are presented as mean (SEM), and were analysed by ANOVA and Dunnett's pairwise multiple comparison t-test. Values differ from the antibody only control: * $P<0.05$,  $P<0.01$, * $P<0.001$.

Within the endometrial cells, the SNIPER MMAE and the SNIPER MMAF ADCs were both significantly more efficacious compared to the other ADCs in HEC1A, HEC1B and Ishikawa cells. There was no significant effect on healthy endometrial cells by any of the ADCs tested (FIG. 20C, D).

EXAMPLE 9

Tamoxifen Upregulates Endometrial RAGE Expression.

RAGE protein expression was measured by Immunohistochemistry in endometrial biopsies from patients diagnosed with endometrial hyperplasia, Type I or Type II endometrial cancer (EC), postmenopausal controls as well as breast cancer patients taking tamoxifen as part of their treatment that have developed, or not, endometrial cancer. 138 patients were grouped as follows: PM (n=25, median=0.2), Hyperplasia (n=21, median=5.5), type I EC (n=18, median=1.5), type II EC (n=17, median=2), TX no EC (n=19, median=4), type I EC plus TX (n=21, median=4) and type II EC plus TX (n=17, median=0.2).

IHC samples were scored blind by three independent observers. Values shown are median IHC scores and statistical analysis was performed using a Mann-Whitney test * $p<0.05$,  $p<0.01$, * $p<0.001$, compared to PM control. Table number 2 below shows between group comparisons.

Figure 21:
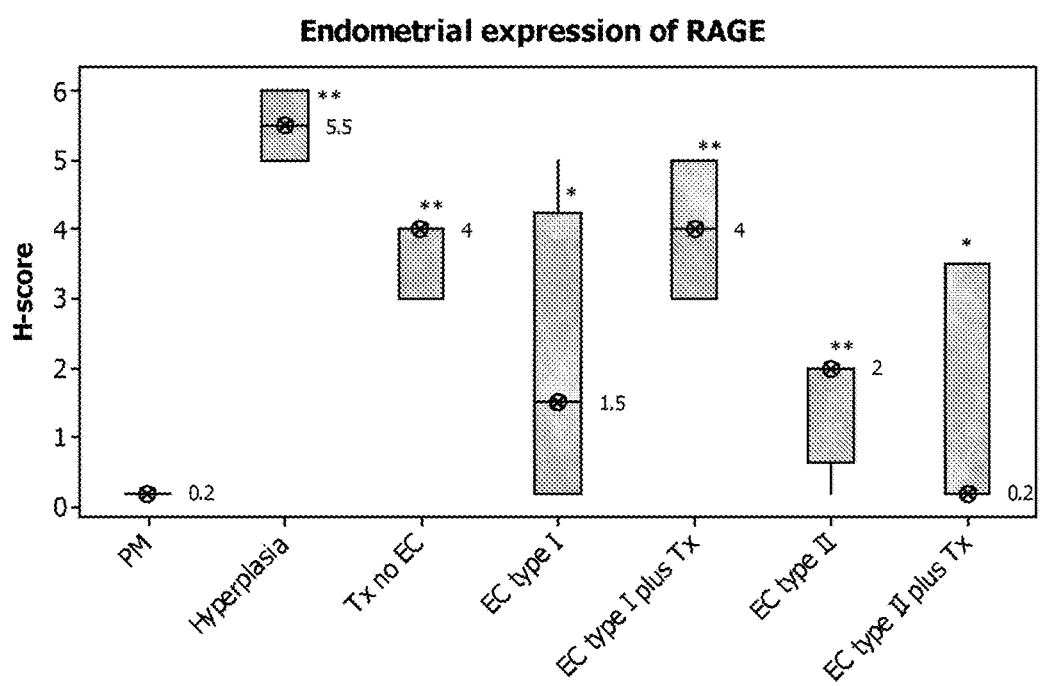
FIG. 21 shows the results of experiments revealing the effect of tamoxifen (Tx) on endometrial expression of RAGE.

The results are shown in FIG. 21. RAGE expression was noted in the membrane and cytoplasm of tumour cells and endometrial cells obtained from hyperplasia patients. PM staining was almost negative. RAGE expression was also observed in the epithelium and stromal cells of the endometrium from breast cancer patients taken tamoxifen that have not developed Endometrial cancer (Tx no EC). Tamoxifen upregulation of RAGE was also observed in endometrium from EC patients compared to endometrium of EC not taking tamoxifen.

Estrogen receptor α (ER) expression was also measured and was found to be expressed in all groups. Its expression was used as control for tamoxifen action in EC patients.

TABLE 1

| | | IC50 | | | | | |
|---|---|---|---|---|---|---|---|
| | | SNIPER-MMAE (μg/ml) [Drug only equivalent, μM] | | | SNIPER-MMAF (μg/ml) [Drug only equivalent, μM] | | |
| Tissue | Cell line | 24 h | 48 h | 96 h | 24 h | 48 h | 96 h |
| Endometrium | Healthy | ND | 10.72 [0.22] | 15.19 [0.31] | ND | 7.25 [0.14] | 4.17 [0.08] |
| | HEC1A | 10.34 [0.22] | 4.69 [0.1] | 1.02 [0.02] | 24.11 [0.46] | 0.81 [0.02] | 0.74 [0.02] |
| | HEC1B | 29.04 [0.61] | 8.65 [0.18] | 5.67 [0.12] | ND | 1.96 [0.04] | 1.27 [0.02] |
| | HEC50 | ND | 7.64 [0.16] | 2.18 [0.05] | 17.82 [0.33] | 0.86 [0.02] | 0.94 [0.02] |
| | Ishikawa | 31.02 [0.65] | 9.54 [0.2] | 3.86 [0.08] | 16.7 [0.32] | 6.48 [0.12] | 2.42 [0.04] |
| Ovary | Healthy | ND | ND | 41.02 [0.86] | ND | 14.36 [0.27] | 4.87 [0.09] |
| | TOV112D | 22.6 [0.47] | 16.17 [0.34] | 0.54 [0.01] | ND | 2.51 [0.05] | 0.59 [0.01] |

ND = not determined within the ADC concentration range used (0.01 to 100 μg/ml)

TABLE 2

| Comparisons RAGE expression | EC type II plus Tx | EC type I | EC type II | TX no EC | Hyperplasia | PM |
|---|---|---|---|---|---|---|
| EC type I plus Tx | 0.0320 | 0.0500 | 0.0003 | 0.5419 | 0.0093 | 0.0002 |
| EC type II plus Tx | | 0.3572 | 0.4442 | 0.0074 | 0.0007 | 0.0450 |
| EC type I | | | 0.8008 | 0.2476 | 0.0015 | 0.0301 |
| EC type II | | | | 0.0003 | 0.0014 | 0.0072 |
| TX no EC | | | | | 0.0011 | 0.0003 |
| Hyperplasia | | | | | | 0.0011 |

Sequences Referred to Herein

| SEQ ID NO | |
|---|---|
| 1 | MAAGTAVGAWVLVLSLWGAVVGAQNITARIGEPLVLKCKGAPKKPPQRLEWKLNTGRTEAWKVLSPQGGGPWDSVARVLPNGSLFLPAVGIQDEGIFRCQAMNRNGKETKSNYRVRVYQIPGKPEIVDSASELTAGVPNKVGTCVSEGSYPAGTLSWHLDGKPLVPNEKGVSVKEQTRRHPETGLFTLQSELMVTPARGGDPRPTFSCSFSPGLPRHRALRTAPIQPRVWEPVPLEEVQLVVEPEGGAVAPGGTVTLTCEVPAQPSPQIHWMKDGVPLPLPPSPVLILPEIGPQDQGTYSCVATHSSHGPQESRAVSISIIEPGEEGPTAGSVGGSGLGTLALALGILGGLGTAALLIGVILWQRRQRRGEERKAPENQEEEEERAELNQSEEPEAGESSIGGP |
| 2 | MAAGTAVGAWVLVLSLWGAVVGAQNITARIGEPLVLKCKGAPKKPPQRLEWKLNTGRTEAWKVLSPQGGGPWDSVARVLPNGSLFLPAVGIQDEGIFRCQAMNRNGKETKSNYRVRVYQIPGKPEIVDSASELTAGVPNKVGICVSEGSYPAGILSWHLDGKPLTRRHPETGLFTLQSELMVTPARGGDPRPTFSCSFSPGLPRHRALRTAPIQPRVWEPVPLEEVQLVVEPEGGAVAPGGIVTLICEVPAQPSPQIHWMKDGVPLPLPPSPVLILPEIGPQDQGTYSCVATHSSHGPQESRAVSISIIEPGEEGPTAGEGFDKVREAEDSPQHM |
| 3 | MAAGTAVGAWVLVLSLWGAVVGAQNITARIGEPLVLKCKGAPKKPPQRLEWKLNTGRTEAWKVLSPQGGGPWDSVARVLPNGSLFLPAVGIQDEGIFRCQAMNRNGKETKSNYRVRVYQIPGKPEIVDSASELTAGVPNKVVEESRRSRKRPCEQEVGICVSEGSYPAGILSWHLDGKPLVPNEKGVSVKEQTRRHPETGLFTLQSELMVTPARGGDPRPTFSCSFSPGLPRHRALRTAPIQPRVWEPVPLEEVQLVVEPEGGAVAPGGIVTLICEVPAQPSPQIHWMKDGVPLPLPPSPVLILPEIGPQDQGTYSCVATHSSHGPQESRAVSISIIEPGEEGPTAGSVGGSGLGTLALALGILGGLGTAALLIGVILWQRRQRRGEERKAPENQEEEEERAELNQSEEPEAGESSTGGP |
| 4 | MAAGTAVGAWVLVLSLWGAVVGAQNITARIGEPLVLKCKGAPKKPPQRLEWKLGGGPWDSVARVLPNGSLFLPAVGIQDEGIFRCQAMNRNGKETKSNYRVRVYQIPGKPEIVDSASELTAGVPNKVGICVSEGSYPAGILSWHLDGKPLVPNEKGVSVKEQTRRHPETGLFTLQSELMVTPARGGDPRPTFSCSFSPGLPRHRALRTAPIQPRVWEPVPLEEVQLVVEPEGGAVAPGGIVTLICEVPAQPSPQIHWMKDGVPLPLPPSPVLILPEIGPQDQGTYSCVATHSSHGPQESRAVSISIIEPGEEGPTAGSVGGSGLGTLALALGILGGLGTAALLIGVILWQRRQRRGEERKAPENQEEEEERAELNQSEEPEAGESSTGGP |
| 5 | MAAGTAVGAWVLVLSLWGAVVGAQNITARIGEPLVLKCKGAPKKPPQRLEWKLNTGRTEAWKVLSPQGGGPWDSVARVLPNGSLFLPAVGIQDEGIFRCQAMNRNGKETKSNYRVRVYQIPGKPEIVDSASELTAGVPNKVVEESRRSRKRPCEQEVGICVSEGSYPAGILSWHLDGKPLVPNEKGVSVKEQTRRHPETGLFTLQSELMVTPARGGDPRPTFSCSFSPGLPRHRALRTAPIQPRVWEPVPLEEVQLVVEPEGGAVAPGGIVTLICEVPAQPSPQIHWMKDGVPLPLPPSPVLILPEIGPQDQGTYSCVATHSSHGPQESRAVSISIIEPGEEGPTAGEGFDKVREAEDSPQHM |
| 6 | MAAGTAVGAWVLVLSLWGAVVGAQNITARIGEPLVLKCKGAPKKPPQRLEWKLNTGRTEAWKVLSPQGGGPWDSVARVLPNGSLFLPAVGIQDEGIFRCQAMNRNGKETKSNYRVRVYQIPGKPEIVDSASELTAGVPNKVGICVSEGSYPAGILSWHLDGKPLVPNEKGVSVKEQTRRHPETGLFTLQSELMVTPARGGDPRPTFSCSFSPGLPRHRALRTAPIQPRVWEPVPLEEVQLVVEPEGGAVAPGGIVTLICEVPAQPSPQIHWMKDGLRTREPTAVWPPIPATGPRKAVLSASASSNQARRGQLQVRGLIKSGKQKIAPNTCDWGDGQQERNGRPQKTRRKRR |
| 7 | MAAGTAVGAWVLVLSLWGAVVGAQNITARIGEPLVLKCKGAPKKPPQRLEWKLNTGRTEAWKVLSPQGGGPWDSVARVLPNGSLFLPAVGIQDEGIFRCQAMNRNGKETKSNYRVRVYQIPGKPEIVDSASELTAGVPNKVGICVSEGSYPAGILSWHLDGKPLVPNEKGVSVKEQTRRHPETGLFTLQSELMVTPARGGDPRPTFSCSFSPGLPRHRALRTAPIQPRVWEPVPLEEVQLVVEPEGGAVAPGGIVTLICEVPAQPSPQIHWMKDGVPLPLPPSPVLILPEIGPQDQGTYSCVATHSSHGPQESRAVSISIIEPGEEGPTAGEGFDKVREAEDSPQHM |
| 8 | MAAGTAVGAWVLVLSLWGAVVGAQNITARIGEPLVLKCKGAPKKPPQRLEWKLGGGPWDSVARVLPNGSLFLPAVGIQDEGIFRCQAMNRNGKETKSNYRVRVYQIPGKPEIVDSASELTAGVPNKVGICVSEGSYPAGILSWHLDGKPLVPNEKGVSVKEQTRRHPETGLFTLQSELMVTPARGGDPRPTFSCSFSPGLPRHRALRTAPIQPRVWEPVPLEEVQLVVEPEGGAVAPGGIVTLICEVPAQPSPQIHWMKDVSDLERGAGRTRRGGANCRLCGRIRAGNSSPGPGDPGRPGDSRPAHWGHLVAKAATPRRGEEGPRKPGGRGGACRTESVGGT |
| 9 | MAAGTAVGAWVLVLSLWGAVVGAQNITARIGEPLVLKCKGAPKKPPQRLEWKLNTGRTEAWKVLSPQGGGPWDSVARVLPNGSLFLPAVGIQDEGIFRCQAMNRNGKETKSNYRVRVYQIPGKPEIVDSASELTAGVPNKVGICVSEGSYPAGILSWHLDGKPLVPNEKGVSVKEQTRRHPETGLFTLQSELMVTPARGGDPRPTFSCSFSPGLPRHRALRTAPIQPRVWEPVPLEEVQLVVEPEGGAVAPGGIVTLICEVPAQPSPQIHWMKDNQARRGQLQVRGLIKSGKQKIAPNTCDWGDGQQERNGRPQKTRRKRRSVQN |
| 10 | MAAGTAVGAWVLVLSLWGAVVGAQNITARIGEPLVLKCKGAPKKPPQRLEWKLNTGRTEAWKVLSPQGGGPWDSVARVLPNGSLFLPAVGIQDEGIFRCQAMNRNGKETKSNYRVRVYQIPGKPEIVDSASELTAGVPNKVGICVSEGSYPAGILSWHLDGKPLVPNEKGVSVKEQTRRHPETGLFTLQSELMVTPARGGDPRPTFSCSFSPGLPRHRALRTAPIQPRVWEPVPLEEVQLVVEPEGGAVAPGGIVTLICEVPAQPSPQIHWMKDGVPLPLPPSPVLILPEIGPQDQGTYSCVATHSSHGPQESRAVSISIIEPGEEGPTAGEGFDKVREAEDSPQHM |
| 11 | MAAGTAVGACASGGGPIGGGARRWSSSSWWNRNPDL |
| 12 | MAAGTAVGAWVLVLSLWGAVVGAQNITARIGEPLVLKCKGAPKKPPQRLEWKLNTGRTEAWKVLSPQGGGPWDSVARVLPNGSLFLPAVGIQDEGIFRCQAMNRNGKETKSNWWWSQKVEQ |
| 13 | MAAGTAVGAWVLVLSLWGAVVGAQNITARIGEPLVLKCKGAPKKPPQRLEWKLNTGRTEAWKVLSPQGGGPWDSVARVLPNGSLFLPAVGIQDEGILGGLGTAALLIGVILWQRRQRRGEERKAPENQEEEEERAELNQSEEPEAGESSTGGP |

| SEQ ID NO | |
|---|---|
| 14 | MVTPARGGDPRPTFSCSFSPGPPRHRALRTAPIQPRVWEPVPLEEVQLVVEPEGGAVAPGGIVTLICEVPAQPSPQIHWMKDGVPLPLPPSPVLI LPEIGPQDQGTYSCVATHSSHGPQESRAVSISIIEPGEEGPTAGEGFDKVREAEDSPQHM |
| 15 | MERRPSPITESVSTSLRTFTITASDWIFPPSEIPGKPEIVDSASELTAGVPNKVGICVSEGSYPAGILSWHLDGKPLVPNEKGVSVKEQTRRHPE TGLFTLQSELMVTPARGGDPRPTFSCSFSPGLPRHRALRTAPIQPRVWEPVPLEEVQLVVEPEGGAVAPGGIVTLICEVPAQPSPQIHWMKDGVP LPLPPSPVLILPEIGPQDQGTYSCVATHSSHGPQESRAVSISIIEPGEEGPTAGEGFDKVREAEDSPQHM |
| 16 | MNRNGKETKSNYRVRVYQIPGKPEIVDSASELTAGVPNKVGICVSEGSYPAGILSWHLDGKPLVPNEKGVSVKEQTRRHPETGLFTLQSELMVTP ARGGDPRPTFSCSFSPGLPRHRALRTAPIQPRVWEPVPLEEVQLVVEPEGGVVAPGGIVTLICEVPAQPSPQIHWMKDGVPLPLPPSPVLILPEI GPQDQGTYSCVATHSSHGPQESRAVSISIIEPGEEGPTAGEGFDKVREAEDSPQHM |
| 17 | MERRPSPITESVSTSLRTFTITASDWIFPPSEIPGKPEIVDSASELTAGVPHKVGICVSEGSYPAGILSWHLDGKPLVPNEKGVSVKEQTRRHPE TGLFTLQSELMVTPARGGDPRPTFSCSFSPGLPRHRALRTAPIQPRVWEPVPLEEVQLVVEPEGGAVAPGGIVTLICEVPAQPSPQIHWMKDGVP LPLPPSPVLILPEIGPQDQGTYSCVATHSSHGPQESRAVSISIIEPGEEGPTAGEGFDKVREAEDSPQHM |
| 18 | MGSPWCLMRRGVSVKEQTRRHPETGLFTLQSELMVTPARGGDPRPTFSCSFSPGLPRHRALRTAPIQPRVWEPVPLEEVQLVVEPEGGAVAPGGI VTLICEVPAQPSPQIHWMKDGVPLPLPPSPVLILPEIGPQDQGTYSCVATHSSHGPQESRAVSISIIEPGEEGPTAGSVGGSGLGTLALALGILG GLGTAALLIGVILWQRRQRRGEERKAPENQEEEEERAELNQSEEPEAGESSTGGP |
| 19 | MNRNGKETKSNYRVRVYQIPGKPEIVDSASELTAGVPNKVGICVSEGSYPAGILSWHLDGKPLVPNEKGVSVKEQTRRHPETGLFTLQSELMVTP ARGGDPRPTFSCSFSPGLPRHRALRTAPIQPRVWEPVPLEEVQLVVEPEGGAVAPGGIVTLICEVPAQPSPQIHWMKDGVPLPLPPSPVLILPEI GPQDQGTYSCVATHSSHGPQESRAVSISIIEPGEEGPTAGEGFDKVREAEDSPQHM |
| 20 | MAAGTAVGAWVLVLSLWGAVVGAQNITARIGEPLVLKCKGAPKKPPQRLEWKLNTGRTEAWKVLSPQGGGPWDSVARVLPNGSLFLPAVGIQDEG IFRCQAMNRNGKETKSNYRVRVYQIPGKPEIVDSASELTAGVPNKVGICVSEGSYPAGILSWHLDGKPLVPNEKGVSVKEQTRRHPETGLFTLQS ELMVTPARGGDPRPTFSCSFSPGLPRHRALRTAPIQPRVWGEHRWGGPQAHVSTFWKSDP |
| 21 | MAAGTAVGAWVLVLSLWGAVVGAQNITARIGEPLVLKCKGAPKKPPQRLEWKLNTGRTEAWKVLSPQGGGPWDSVARVLPNGSLFLPAVGIQDEG IFRCQAMNRNGKETKSNWWWSQKVEQ |
| 22 | MAAGTAVGAWVLVLSLWGAVVGAQNITARIGEPLVLKCKGAPKKPPQRLEWKLNTGRTEAWKVLSPQGGGPWDSVARVLPNGSLFLPAVGIQDEG IFRCQAMNRNGKETKSNYRVRVYQIPGKPEIVDSASELTAGVPNKVGICVSEGSYPAGILSWHLDGKPLVPNEKGVSVKEQTRRHPETGLFTLQS ELMVTPARGGDPRPTFSCSFSPGLPRHRALRTAPIQPRVWEPVPLEEVQLVVEPEGGAVAPGGIVTLICEVPAQPSPQIHWMKDGVPLPLPPSPV LILPEIGPQDQGTYSCVATHSSHGPQESRAVSISIIEPGEEGPTAGSVGGSGLGTLALALGILGGLGTAALLIGVILWQRRQRRAELNQSEEPEA GESSTGGP |
| 23 | MNRNGKETKSNYRVRVYQIPGKPEIVDSASELTAGVPNKVGICVSEGSYPAGILSWHLDGKPLVPNEKGVSVKEQTRRHPETGLFTLQSELMVTP ARGGDPRPTFSCSFSPGLPRHRALRTAPIQPRVWGEHRWGGPQAHVSTFWKSDP |
| 24 | SISIIEPGEEGPTAGSVGGSGLGTLALA |
| 25 | QVQLQQSGAELVKPGASVKLSCKTSGYTFTNYYIYWVIQRPGHGLEWIGEINPSNGGINFSERFKSRAKLTVDKPSSTAYMQLSSLTSDDSAVYY CTINFDYWGQGSTLTVSS |
| 26 | DVLMTQTPLSLPVSLGDQASMSCRSSQNIVHNNGNTYLQWYLQKPGQSPKLLIYQVSNRFFGVPDRFSGSGSGTDFTLKISRVEAEDLGVYYCFQ GSHLPLTFGAGTKLELK |
| 27 | QVQLLQPGAELVRPGASVRLSCKASGYTFTSYWINWVKQRPGQGLEWIGNIYPSDSYTNYNQKFKDKATLTVDKSSSTAYMQLSSPTSEDSAVYY CAREGYWGQGTLVTVSA |
| 28 | ELVMTQSPLTLSVTIGQPASISCKSGQSLLYSNGKTYLYWLLQRPGQSPKRLIYLVSKLDSGVPDRFTGSGSGTDFTLKISRVEAEDLGVYYCVQ GTHFPYTFGGGTKLEIK |

REFERENCES

1. Neeper, M. et al. Cloning and expression of a cell surface receptor for advanced glycosylation end products of proteins. *J Biol Chem* 267, 14998-15004 (1992).
2. Sugaya, K. et al. Three genes in the human MHC class III region near the junction with the class II: gene for receptor of advanced glycosylation end products, PBX2 homeobox gene and a notch homolog, human counterpart of mouse mammary tumor gene int-3. *Genomics* 23, 408-419, doi:S0888754384715175 [pii] (1994).
3. Fritz, G. RAGE: a single receptor fits multiple ligands. *Trends Biochem Sci* 36, 625-632, doi:10.1016/j.tibs.2011.08.008S0968-0004(11)00137-X [pii] (2011).
4. Bierhaus, A. et al. Diabetes-associated sustained activation of the transcription factor nuclear factor-kappaB. *Diabetes* 50, 2792-2808 (2001).
5. Verdier, Y., Zarandi, M. & Penke, B. Amyloid beta-peptide interactions with neuronal and glial cell plasma membrane: binding sites and implications for Alzheimer's disease. *J Pept Sci* 10, 229-248, doi:10.1002/psc.573 (2004).
6. Williams, J. H. & Ireland, H. E. Sensing danger—Hsp72 and HMGB1 as candidate signals. *J Leukoc Biol* 83, 489-492, doi:jlb.0607356 [pii]10.1189/jlb.0607356 (2008).
7. Chiodoni, C., Colombo, M. P. & Sangaletti, S. Matricellular proteins: from homeostasis to inflammation, cancer, and metastasis. *Cancer Metastasis Rev* 29, 295-307, doi:10.1007/s10555-010-9221-8 (2010).
8. Sevillano, N. et al. Internalization of the receptor for advanced glycation end products (RAGE) is required to mediate intracellular responses. *J Biochem* 145, 21-30, doi:10.1093/jb/mvn137mvn137 [pii] (2009).

9 Rojas, A. et al. The receptor for advanced glycation end-products: a complex signaling scenario for a promiscuous receptor. *Cell Signal* 25, 609-614, doi:10.1016/j.cellsig.2012.11.02250898-6568(12)00325-7 [pii] (2013).
10 Turovskaya, O. et al. RAGE, carboxylated glycans and S100A8/A9 play essential roles in colitis-associated carcinogenesis. *Carcinogenesis* 29, 2035-2043, doi:10.1093/carcin/bgn188bgn188 [pii] (2008).
11 Gebhardt, C. et al. RAGE signaling sustains inflammation and promotes tumor development. *J Exp Med* 205, 275-285, doi:10.1084/jem.20070679jem.20070679 [pii] (2008).
12 Taguchi, A. et al. Blockade of RAGE-amphoterin signalling suppresses tumour growth and metastases. *Nature* 405, 354-360, doi:10.1038/35012626 (2000).
13 Hiwatashi, K. et al. A novel function of the receptor for advanced glycation end-products (RAGE) in association with tumorigenesis and tumor differentiation of HCC. *Ann Surg Oncol* 15, 923-933, doi:10.1245/s10434-007-9698-8 (2008).
14 Liliensiek, B. et al. Receptor for advanced glycation end products (RAGE) regulates sepsis but not the adaptive immune response. *Journal of Clinical Investigation* 113, 1641-1650, doi:Doi 10.1172/Jci200418704 (2004).
15 Zhang, L. et al. Receptor for advanced glycation end products is subjected to protein ectodomain shedding by metalloproteinases. *J Biol Chem* 283, 35507-35516, doi: 10.1074/jbc.M806948200M806948200 [pii] (2008).
16 Dykxhoorn, D. M. RNA interference as an anticancer therapy: a patent perspective. *Expert Opin Ther Pat* 19, 475-491, doi:Doi 10.1517/13543770902838008 (2009).
17 Ramachandran, P. V. & Ignacimuthu, S. RNA Interference as a Plausible Anticancer Therapeutic Tool. *Asian Pac J Cancer P* 13, 2445-2452, doi:Doi 10.7314/Apjcp.2012.13.6.2445 (2012).
18 Ducry, L. & Stump, B. Antibody-Drug Conjugates: Linking Cytotoxic Payloads to Monoclonal Antibodies. *Bioconjugate Chem* 21, 5-13, doi:Doi 10.1021/Bc9002019 (2010).
19 Doronina, S. O. et al. Enhanced activity of monomethylauristatin F through monoclonal antibody delivery: effects of linker technology on efficacy and toxicity. *Bioconjug Chem* 17, 114-124, doi:10.1021/bc0502917 (2006).
20 Graf, I. Remington's Pharmaceutical Sciences, 17th Ed.: 100 Years. Hrsg. von The Philadelphia Coll. of Pharmacy and Science, Editor A. R. Gennaro; Mack Publishing Comp., Easton, Pennsylv. 1985, Vertrieb durch J. Wiley & Sons, Ltd, Chichester, W.-Sussex (Engl.), 1984, S. 21×28, £ 85,50 (netto). *Pharmazie in unserer Zeit* 14, 191-191, doi:10.1002/pauz.19850140607 (1985).

---

The invention claimed is:

1. A method for treating a gynaecological cancer, wherein the method comprises administering to a patient in need thereof an effective amount of a therapeutic agent comprising a monoclonal antibody which binds the extracellular domain of Receptor for Advanced Glycation End products (RAGE) linked to an anti-cancer drug.

2. The method of claim 1 wherein the monoclonal antibody is a human or humanised antibody.

3. The method of claim 1 wherein the monoclonal antibody binds a region of RAGE comprising SEQ ID NO: 24.

4. The method of claim 1 wherein the anti-cancer drug is a cytotoxin; a hormone; a cytokine, chemokine, or other cell signaling molecule; or a nucleic acid.

5. The method of claim 1 wherein the monoclonal antibody is linked to the anti-cancer drug by way of a chemical linking group.

6. The method of claim 1 wherein the ratio of drug to monoclonal antibody is from about 1:1 to 1:8.

7. The method of claim 6 wherein the ratio of drug to monoclonal antibody is from about 1:1.5 to 1:3.5.

8. The method of claim 1 wherein the gynaecological cancer is endometrial cancer or ovarian cancer.

9. The method of claim 1 wherein the therapeutic agent is administered together with an anti-hormonal agent that upregulates RAGE in gynaecological cancer.

10. The method of claim 9 wherein the anti-hormonal agent is tamoxifen.

* * * * *

SEQUENCE LISTING

```
<160> NUMBER OF SEQ ID NOS: 28

<210> SEQ ID NO 1
<211> LENGTH: 404
<212> TYPE: PRT
<213> ORGANISM: Homo sapiens
<220> FEATURE:
<223> OTHER INFORMATION: Receptor for advanced glycation end products
      (RAGE)

<400> SEQUENCE: 1

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175
```

```
Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
            195                 200                 205

Ser Phe Ser Pro Gly Leu Pro Arg His Arg Ala Leu Arg Thr Ala Pro
        210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
            245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
            275                 280                 285

Pro Glu Ile Gly Pro Gln Asp Gln Gly Thr Tyr Ser Cys Val Ala Thr
        290                 295                 300

His Ser Ser His Gly Pro Gln Glu Ser Arg Ala Val Ser Ile Ser Ile
305                 310                 315                 320

Ile Glu Pro Gly Glu Glu Gly Pro Thr Ala Gly Ser Val Gly Gly Ser
            325                 330                 335

Gly Leu Gly Thr Leu Ala Leu Ala Leu Gly Ile Leu Gly Gly Leu Gly
            340                 345                 350

Thr Ala Ala Leu Leu Ile Gly Val Ile Leu Trp Gln Arg Arg Gln Arg
            355                 360                 365

Arg Gly Glu Glu Arg Lys Ala Pro Glu Asn Gln Glu Glu Glu Glu Glu
            370                 375                 380

Arg Ala Glu Leu Asn Gln Ser Glu Glu Pro Glu Ala Gly Glu Ser Ser
385                 390                 395                 400

Thr Gly Gly Pro

<210> SEQ ID NO 2
<211> LENGTH: 335
<212> TYPE: PRT
<213> ORGANISM: Homo sapiens
<220> FEATURE:
<223> OTHER INFORMATION: RAGE variant

<400> SEQUENCE: 2

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
            85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125
```

```
Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Thr Arg Arg His Pro Glu Thr Gly Leu Phe Thr Leu
                    165                 170                 175

Gln Ser Glu Leu Met Val Thr Pro Ala Arg Gly Gly Asp Pro Arg Pro
                180                 185                 190

Thr Phe Ser Cys Ser Phe Ser Pro Gly Leu Pro Arg His Arg Ala Leu
            195                 200                 205

Arg Thr Ala Pro Ile Gln Pro Arg Val Trp Glu Pro Val Pro Leu Glu
210                 215                 220

Glu Val Gln Leu Val Val Glu Pro Glu Gly Gly Ala Val Ala Pro Gly
225                 230                 235                 240

Gly Thr Val Thr Leu Thr Cys Glu Val Pro Ala Gln Pro Ser Pro Gln
                    245                 250                 255

Ile His Trp Met Lys Asp Gly Val Pro Leu Pro Leu Pro Pro Ser Pro
                260                 265                 270

Val Leu Ile Leu Pro Glu Ile Gly Pro Gln Asp Gln Gly Thr Tyr Ser
275                 280                 285

Cys Val Ala Thr His Ser Ser His Gly Pro Gln Glu Ser Arg Ala Val
290                 295                 300

Ser Ile Ser Ile Ile Glu Pro Gly Glu Glu Gly Pro Thr Ala Gly Glu
305                 310                 315                 320

Gly Phe Asp Lys Val Arg Glu Ala Glu Asp Ser Pro Gln His Met
                    325                 330                 335

<210> SEQ ID NO 3
<211> LENGTH: 420
<212> TYPE: PRT
<213> ORGANISM: Homo sapiens
<220> FEATURE:
<223> OTHER INFORMATION: RAGE

<400> SEQUENCE: 3

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
                20                  25                  30

Pro Leu Val Leu Lys Cys Lys Gly Ala Pro Lys Lys Pro Pro Gln Arg
            35                  40                  45

Leu Glu Trp Lys Leu Asn Thr Gly Arg Thr Glu Ala Trp Lys Val Leu
        50                  55                  60

Ser Pro Gln Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Val Glu Glu
    130                 135                 140

Ser Arg Arg Ser Arg Lys Arg Pro Cys Glu Gln Glu Val Gly Thr Cys
145                 150                 155                 160
```

Val Ser Glu Gly Ser Tyr Pro Ala Gly Thr Leu Ser Trp His Leu Asp
            165                 170                 175

Gly Lys Pro Leu Val Pro Asn Glu Lys Gly Val Ser Val Lys Glu Gln
        180                 185                 190

Thr Arg Arg His Pro Glu Thr Gly Leu Phe Thr Leu Gln Ser Glu Leu
            195                 200                 205

Met Val Thr Pro Ala Arg Gly Gly Asp Pro Arg Pro Thr Phe Ser Cys
        210                 215                 220

Ser Phe Ser Pro Gly Leu Pro Arg His Arg Ala Leu Arg Thr Ala Pro
225                 230                 235                 240

Ile Gln Pro Arg Val Trp Glu Pro Val Pro Leu Glu Glu Val Gln Leu
            245                 250                 255

Val Val Glu Pro Glu Gly Gly Ala Val Ala Pro Gly Gly Thr Val Thr
        260                 265                 270

Leu Thr Cys Glu Val Pro Ala Gln Pro Ser Pro Gln Ile His Trp Met
        275                 280                 285

Lys Asp Gly Val Pro Leu Pro Leu Pro Pro Ser Pro Val Leu Ile Leu
        290                 295                 300

Pro Glu Ile Gly Pro Gln Asp Gln Gly Thr Tyr Ser Cys Val Ala Thr
305                 310                 315                 320

His Ser Ser His Gly Pro Gln Glu Ser Arg Ala Val Ser Ile Ser Ile
            325                 330                 335

Ile Glu Pro Gly Glu Glu Gly Pro Thr Ala Gly Ser Val Gly Gly Ser
            340                 345                 350

Gly Leu Gly Thr Leu Ala Leu Ala Leu Gly Ile Leu Gly Gly Leu Gly
        355                 360                 365

Thr Ala Ala Leu Leu Ile Gly Val Ile Leu Trp Gln Arg Arg Gln Arg
        370                 375                 380

Arg Gly Glu Glu Arg Lys Ala Pro Glu Asn Gln Glu Glu Glu Glu Glu
385                 390                 395                 400

Arg Ala Glu Leu Asn Gln Ser Glu Glu Pro Glu Ala Gly Glu Ser Ser
            405                 410                 415

Thr Gly Gly Pro
420

<210> SEQ ID NO 4
<211> LENGTH: 390
<212> TYPE: PRT
<213> ORGANISM: Homo sapiens
<220> FEATURE:
<223> OTHER INFORMATION: RAGE Variant

<400> SEQUENCE: 4

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Gly Gly Pro Trp Asp Ser Val Ala Arg Val
    50                  55                  60

Leu Pro Asn Gly Ser Leu Phe Leu Pro Ala Val Gly Ile Gln Asp Glu
65                  70                  75                  80

Gly Ile Phe Arg Cys Gln Ala Met Asn Arg Asn Gly Lys Glu Thr Lys
                85                  90                  95

```
Ser Asn Tyr Arg Val Arg Val Tyr Gln Ile Pro Gly Lys Pro Glu Ile
                100                 105                 110

Val Asp Ser Ala Ser Glu Leu Thr Ala Gly Val Pro Asn Lys Val Gly
            115                 120                 125

Thr Cys Val Ser Glu Gly Ser Tyr Pro Ala Gly Thr Leu Ser Trp His
        130                 135                 140

Leu Asp Gly Lys Pro Leu Val Pro Asn Glu Lys Gly Val Ser Val Lys
145                 150                 155                 160

Glu Gln Thr Arg Arg His Pro Glu Thr Gly Leu Phe Thr Leu Gln Ser
                165                 170                 175

Glu Leu Met Val Thr Pro Ala Arg Gly Gly Asp Pro Arg Pro Thr Phe
            180                 185                 190

Ser Cys Ser Phe Ser Pro Gly Leu Pro Arg His Arg Ala Leu Arg Thr
        195                 200                 205

Ala Pro Ile Gln Pro Arg Val Trp Glu Pro Val Pro Leu Glu Glu Val
210                 215                 220

Gln Leu Val Val Glu Pro Glu Gly Gly Ala Val Ala Pro Gly Gly Thr
225                 230                 235                 240

Val Thr Leu Thr Cys Glu Val Pro Ala Gln Pro Ser Pro Gln Ile His
                245                 250                 255

Trp Met Lys Asp Gly Val Pro Leu Pro Leu Pro Pro Ser Pro Val Leu
            260                 265                 270

Ile Leu Pro Glu Ile Gly Pro Gln Asp Gln Gly Thr Tyr Ser Cys Val
        275                 280                 285

Ala Thr His Ser Ser His Gly Pro Gln Glu Ser Arg Ala Val Ser Ile
        290                 295                 300

Ser Ile Ile Glu Pro Gly Glu Glu Gly Pro Thr Ala Gly Ser Val Gly
305                 310                 315                 320

Gly Ser Gly Leu Gly Thr Leu Ala Leu Ala Leu Gly Ile Leu Gly Gly
                325                 330                 335

Leu Gly Thr Ala Ala Leu Leu Ile Gly Val Ile Leu Trp Gln Arg Arg
            340                 345                 350

Gln Arg Arg Gly Glu Glu Arg Lys Ala Pro Glu Asn Gln Glu Glu Glu
        355                 360                 365

Glu Glu Arg Ala Glu Leu Asn Gln Ser Glu Glu Pro Glu Ala Gly Glu
        370                 375                 380

Ser Ser Thr Gly Gly Pro
385                 390

<210> SEQ ID NO 5
<211> LENGTH: 363
<212> TYPE: PRT
<213> ORGANISM: Homo sapiens

<400> SEQUENCE: 5

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80
```

Asn Gly Ser Leu Phe Leu Pro Ala Val Gly Ile Gln Asp Glu Gly Ile
            85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
            115                 120                 125

Ser Ala Ser Glu Leu Thr Ala Gly Val Pro Asn Lys Val Glu Glu
130                 135                 140

Ser Arg Arg Ser Arg Lys Arg Pro Cys Glu Gln Val Gly Thr Cys
145                 150                 155                 160

Val Ser Glu Gly Ser Tyr Pro Ala Gly Thr Leu Ser Trp His Leu Asp
            165                 170                 175

Gly Lys Pro Leu Val Pro Asn Glu Lys Gly Val Ser Val Lys Glu Gln
            180                 185                 190

Thr Arg Arg His Pro Glu Thr Gly Leu Phe Thr Leu Gln Ser Glu Leu
            195                 200                 205

Met Val Thr Pro Ala Arg Gly Gly Asp Pro Arg Pro Thr Phe Ser Cys
            210                 215                 220

Ser Phe Ser Pro Gly Leu Pro Arg His Arg Ala Leu Arg Thr Ala Pro
225                 230                 235                 240

Ile Gln Pro Arg Val Trp Glu Pro Val Pro Leu Glu Glu Val Gln Leu
            245                 250                 255

Val Val Glu Pro Glu Gly Gly Ala Val Ala Pro Gly Gly Thr Val Thr
            260                 265                 270

Leu Thr Cys Glu Val Pro Ala Gln Pro Ser Pro Gln Ile His Trp Met
            275                 280                 285

Lys Asp Gly Val Pro Leu Pro Leu Pro Pro Ser Pro Val Leu Ile Leu
            290                 295                 300

Pro Glu Ile Gly Pro Gln Asp Gln Gly Thr Tyr Ser Cys Val Ala Thr
305                 310                 315                 320

His Ser Ser His Gly Pro Gln Glu Ser Arg Ala Val Ser Ile Ser Ile
            325                 330                 335

Ile Glu Pro Gly Glu Glu Gly Pro Thr Ala Gly Ser Val Gly Gly Ser
            340                 345                 350

Val Arg Glu Ala Glu Asp Ser Pro Gln His Met
            355                 360

<210> SEQ ID NO 6
<211> LENGTH: 351
<212> TYPE: PRT
<213> ORGANISM: Homo sapiens
<220> FEATURE:
<223> OTHER INFORMATION: RAGE variant

<400> SEQUENCE: 6

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
            35                  40                  45

Leu Glu Trp Lys Leu Asn Thr Gly Arg Thr Glu Ala Trp Lys Val Leu
            50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
            85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
            115                 120                 125

Ser Ala Ser Glu Leu Thr Ala Gly Val Pro Asn Lys Val Gly Thr Cys
130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
            165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
            195                 200                 205

Ser Phe Ser Pro Gly Leu Pro Arg His Arg Ala Leu Arg Thr Ala Pro
            210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
            245                 250                 255

Leu Thr Cys Glu Val Pro Ala Gln Pro Ser Pro Gln Ile His Trp Met
            260                 265                 270

Lys Asp Gly Leu Arg Thr Arg Glu Pro Thr Ala Val Trp Pro Pro Ile
            275                 280                 285

Pro Ala Thr Gly Pro Arg Lys Ala Val Leu Ser Ala Ser Ala Ser Ser
            290                 295                 300

Asn Gln Ala Arg Arg Gly Gln Leu Gln Val Arg Gly Leu Ile Lys Ser
305                 310                 315                 320

Gly Lys Gln Lys Ile Ala Pro Asn Thr Cys Asp Trp Gly Asp Gly Gln
            325                 330                 335

Gln Glu Arg Asn Gly Arg Pro Gln Lys Thr Arg Lys Arg Arg
            340                 345                 350

<210> SEQ ID NO 7
<211> LENGTH: 347
<212> TYPE: PRT
<213> ORGANISM: Homo sapiens
<220> FEATURE:
<223> OTHER INFORMATION: RAGE variant

<400> SEQUENCE: 7

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
            35                  40                  45

Leu Glu Trp Lys Leu Asn Thr Gly Arg Thr Glu Ala Trp Lys Val Leu
            50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
            85                  90                  95

Phe Arg Cys Gln Ala Met Asn Arg Asn Gly Lys Glu Thr Lys Ser Asn
                100                 105                 110

Tyr Arg Val Arg Val Tyr Gln Ile Pro Gly Lys Pro Glu Ile Val Asp
                115                 120                 125

Ser Ala Ser Glu Leu Thr Ala Gly Val Pro Asn Lys Val Gly Thr Cys
130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
                180                 185                 190

Met Val Thr Pro Ala Arg Gly Gly Asp Pro Arg Pro Thr Phe Ser Cys
                195                 200                 205

Ser Phe Ser Pro Gly Leu Pro Arg His Arg Ala Leu Arg Thr Ala Pro
                210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
                260                 265                 270

Lys Asp Gly Val Pro Leu Pro Leu Pro Pro Ser Pro Val Leu Ile Leu
                275                 280                 285

Pro Glu Ile Gly Pro Gln Asp Gln Gly Thr Tyr Ser Cys Val Ala Thr
                290                 295                 300

His Ser Ser His Gly Pro Gln Glu Ser Arg Ala Val Ser Ile Ser Ile
305                 310                 315                 320

Ile Glu Pro Gly Glu Glu Gly Pro Thr Ala Gly Glu Gly Phe Asp Lys
                325                 330                 335

Val Arg Glu Ala Glu Asp Ser Pro Gln His Met
                340                 345

```
<210> SEQ ID NO 8
<211> LENGTH: 342
<212> TYPE: PRT
<213> ORGANISM: Homo sapiens
<220> FEATURE:
<223> OTHER INFORMATION: Rage variant

<400> SEQUENCE: 8
```

Met Ala Ala Gly Thr Ala Val Gly Ala Trp Val Leu Val Leu Ser Leu
1                   5                   10                  15

Trp Gly Ala Val Val Gly Ala Gln Asn Ile Thr Ala Arg Ile Gly Glu
                20                  25                  30

Pro Leu Val Leu Lys Cys Lys Gly Ala Pro Lys Lys Pro Pro Gln Arg
                35                  40                  45

Leu Glu Trp Lys Leu Gly Gly Gly Pro Trp Asp Ser Val Ala Arg Val
                50                  55                  60

Leu Pro Asn Gly Ser Leu Phe Leu Pro Ala Val Gly Ile Gln Asp Glu
65                  70                  75                  80

Gly Ile Phe Arg Cys Gln Ala Met Asn Arg Asn Gly Lys Glu Thr Lys
                85                  90                  95

Ser Asn Tyr Arg Val Arg Val Tyr Gln Ile Pro Gly Lys Pro Glu Ile
                100                 105                 110

```
Val Asp Ser Ala Ser Glu Leu Thr Ala Gly Val Pro Asn Lys Val Gly
        115                 120                 125
Thr Cys Val Ser Glu Gly Ser Tyr Pro Ala Gly Thr Leu Ser Trp His
130                 135                 140
Leu Asp Gly Lys Pro Leu Val Pro Asn Glu Lys Gly Val Ser Val Lys
145                 150                 155                 160
Glu Gln Thr Arg Arg His Pro Glu Thr Gly Leu Phe Thr Leu Gln Ser
                165                 170                 175
Glu Leu Met Val Thr Pro Ala Arg Gly Gly Asp Pro Arg Pro Thr Phe
            180                 185                 190
Ser Cys Ser Phe Ser Pro Gly Leu Pro Arg His Arg Ala Leu Arg Thr
        195                 200                 205
Ala Pro Ile Gln Pro Arg Val Trp Glu Pro Val Pro Leu Glu Glu Val
    210                 215                 220
Gln Leu Val Val Glu Pro Glu Gly Gly Ala Val Ala Pro Gly Gly Thr
225                 230                 235                 240
Val Thr Leu Thr Cys Glu Val Pro Ala Gln Pro Ser Pro Gln Ile His
                245                 250                 255
Trp Met Lys Asp Val Ser Asp Leu Glu Arg Gly Ala Gly Arg Thr Arg
            260                 265                 270
Arg Gly Gly Ala Asn Cys Arg Leu Cys Gly Arg Ile Arg Ala Gly Asn
        275                 280                 285
Ser Ser Pro Gly Pro Gly Asp Pro Gly Arg Pro Gly Asp Ser Arg Pro
    290                 295                 300
Ala His Trp Gly His Leu Val Ala Lys Ala Thr Pro Arg Arg Gly
305                 310                 315                 320
Glu Glu Gly Pro Arg Lys Pro Gly Gly Arg Gly Ala Cys Arg Thr
                325                 330                 335
Glu Ser Val Gly Gly Thr
            340

<210> SEQ ID NO 9
<211> LENGTH: 325
<212> TYPE: PRT
<213> ORGANISM: Homo sapiens
<220> FEATURE:
<223> OTHER INFORMATION: Rage variant

<400> SEQUENCE: 9

Met Ala Ala Gly Thr Ala Val Gly Ala Trp Val Leu Val Leu Ser Leu
1               5                   10                  15
Trp Gly Ala Val Val Gly Ala Gln Asn Ile Thr Ala Arg Ile Gly Glu
            20                  25                  30
Pro Leu Val Leu Lys Cys Lys Gly Ala Pro Lys Lys Pro Pro Gln Arg
        35                  40                  45
Leu Glu Trp Lys Leu Asn Thr Gly Arg Thr Glu Ala Trp Lys Val Leu
    50                  55                  60
Ser Pro Gln Gly Gly Gly Pro Trp Asp Ser Val Ala Arg Val Leu Pro
65                  70                  75                  80
Asn Gly Ser Leu Phe Leu Pro Ala Val Gly Ile Gln Asp Glu Gly Ile
                85                  90                  95
Phe Arg Cys Gln Ala Met Asn Arg Asn Gly Lys Glu Thr Lys Ser Asn
            100                 105                 110
Tyr Arg Val Arg Val Tyr Gln Ile Pro Gly Lys Pro Glu Ile Val Asp
        115                 120                 125
```

```
Ser Ala Ser Glu Leu Thr Ala Gly Val Pro Asn Lys Val Gly Thr Cys
            130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
            260                 265                 270

Lys Asp Asn Gln Ala Arg Arg Gly Gln Leu Gln Val Arg Gly Leu Ile
        275                 280                 285

Lys Ser Gly Lys Gln Lys Ile Ala Pro Asn Thr Cys Asp Trp Gly Asp
    290                 295                 300

Gly Gln Gln Glu Arg Asn Gly Arg Pro Gln Lys Thr Arg Arg Lys Arg
305                 310                 315                 320

Arg Ser Val Gln Asn
            325

<210> SEQ ID NO 10
<211> LENGTH: 347
<212> TYPE: PRT
<213> ORGANISM: Homo sapiens

<400> SEQUENCE: 10

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Pro Trp Asp Ser Val Ala Arg Val Leu Pro Asn
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
```

```
                        165                 170                 175
Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
            195                 200                 205

Ser Phe Ser Pro Gly Leu Pro Arg His Arg Ala Leu Arg Thr Ala Pro
            210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
            245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
            275                 280                 285

Pro Glu Ile Gly Pro Gln Asp Gln Gly Thr Tyr Ser Cys Val Ala Thr
            290                 295                 300

His Ser Ser His Gly Pro Gln Glu Ser Arg Ala Val Ser Ile Ser Ile
305                 310                 315                 320

Ile Glu Pro Gly Glu Glu Pro Thr Ala Gly Glu Gly Phe Asp Lys
            325                 330                 335

Val Arg Glu Ala Glu Asp Ser Pro Gln His Met
            340                 345

<210> SEQ ID NO 11
<211> LENGTH: 36
<212> TYPE: PRT
<213> ORGANISM: Homo sapiens
<220> FEATURE:
<223> OTHER INFORMATION: Rage variant

<400> SEQUENCE: 11

Met Ala Ala Gly Thr Ala Val Gly Ala Cys Ala Ser Gly Gly Gly Pro
1               5                   10                  15

Ile Gly Gly Gly Ala Arg Arg Trp Ser Ser Ser Ser Trp Trp Asn Arg
            20                  25                  30

Asn Pro Asp Leu
        35

<210> SEQ ID NO 12
<211> LENGTH: 121
<212> TYPE: PRT
<213> ORGANISM: Homo sapiens
<220> FEATURE:
<223> OTHER INFORMATION: RAGE variant

<400> SEQUENCE: 12

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
            35                  40                  45

Leu Glu Trp Lys Leu Asn Thr Gly Arg Thr Glu Ala Trp Lys Val Leu
        50                  55                  60

Ser Pro Gln Gly Gly Gly Pro Trp Asp Ser Val Ala Arg Val Leu Pro
65                  70                  75                  80
```

```
Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Trp Trp Trp Ser Gln Lys Val Glu Gln
        115                 120

<210> SEQ ID NO 13
<211> LENGTH: 153
<212> TYPE: PRT
<213> ORGANISM: Homo sapiens
<220> FEATURE:
<223> OTHER INFORMATION: Rage variant

<400> SEQUENCE: 13

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Leu Gly Gly Leu Gly Thr Ala Ala Leu Leu Ile Gly Val Ile Leu Trp
            100                 105                 110

Gln Arg Arg Gln Arg Arg Gly Glu Glu Arg Lys Ala Pro Glu Asn Gln
        115                 120                 125

Glu Glu Glu Glu Glu Arg Ala Glu Leu Asn Gln Ser Glu Glu Pro Glu
    130                 135                 140

Ala Gly Glu Ser Ser Thr Gly Gly Pro
145                 150

<210> SEQ ID NO 14
<211> LENGTH: 155
<212> TYPE: PRT
<213> ORGANISM: Homo sapiens
<220> FEATURE:
<223> OTHER INFORMATION: Rage variant

<400> SEQUENCE: 14

Met Val Thr Pro Ala Arg Gly Gly Asp Pro Arg Pro Thr Phe Ser Cys
1               5                   10                  15

Ser Phe Ser Pro Gly Pro Arg His Arg Ala Leu Arg Thr Ala Pro
            20                  25                  30

Ile Gln Pro Arg Val Trp Glu Pro Val Pro Leu Glu Glu Val Gln Leu
        35                  40                  45

Val Val Glu Pro Glu Gly Gly Ala Val Ala Pro Gly Gly Thr Val Thr
    50                  55                  60

Leu Thr Cys Glu Val Pro Ala Gln Pro Ser Pro Gln Ile His Trp Met
65                  70                  75                  80

Lys Asp Gly Val Pro Leu Pro Leu Pro Pro Ser Pro Val Leu Ile Leu
                85                  90                  95

Pro Glu Ile Gly Pro Gln Asp Gln Gly Thr Tyr Ser Cys Val Ala Thr
            100                 105                 110
```

His Ser Ser His Gly Pro Gln Glu Ser Arg Ala Val Ser Ile Ser Ile
        115                 120                 125

Ile Glu Pro Gly Glu Glu Gly Pro Thr Ala Gly Gly Phe Asp Lys
130                 135                 140

Val Arg Glu Ala Glu Asp Ser Pro Gln His Met
145                 150                 155

<210> SEQ ID NO 15
<211> LENGTH: 260
<212> TYPE: PRT
<213> ORGANISM: Homo sapiens
<220> FEATURE:
<223> OTHER INFORMATION: Rage variant

<400> SEQUENCE: 15

Met Glu Arg Arg Pro Ser Pro Thr Thr Glu Ser Val Ser Thr Ser Leu
1               5                   10                  15

Arg Thr Phe Thr Ile Thr Ala Ser Asp Trp Ile Phe Pro Pro Ser Glu
            20                  25                  30

Ile Pro Gly Lys Pro Glu Ile Val Asp Ser Ala Ser Glu Leu Thr Ala
        35                  40                  45

Gly Val Pro Asn Lys Val Gly Thr Cys Val Ser Glu Gly Ser Tyr Pro
50                  55                  60

Ala Gly Thr Leu Ser Trp His Leu Asp Gly Lys Pro Leu Val Pro Asn
65                  70                  75                  80

Glu Lys Gly Val Ser Val Lys Glu Gln Thr Arg Arg His Pro Glu Thr
                85                  90                  95

Gly Leu Phe Thr Leu Gln Ser Glu Leu Met Val Thr Pro Ala Arg Gly
            100                 105                 110

Gly Asp Pro Arg Pro Thr Phe Ser Cys Ser Phe Ser Pro Gly Leu Pro
        115                 120                 125

Arg His Arg Ala Leu Arg Thr Ala Pro Ile Gln Pro Arg Val Trp Glu
130                 135                 140

Pro Val Pro Leu Glu Glu Val Gln Leu Val Val Glu Pro Gly Gly Gly
145                 150                 155                 160

Ala Val Ala Pro Gly Gly Thr Val Thr Leu Thr Cys Glu Val Pro Ala
                165                 170                 175

Gln Pro Ser Pro Gln Ile His Trp Met Lys Asp Gly Val Pro Leu Pro
            180                 185                 190

Leu Pro Pro Ser Pro Val Leu Ile Leu Pro Glu Ile Gly Pro Gln Asp
        195                 200                 205

Gln Gly Thr Tyr Ser Cys Val Ala Thr His Ser Ser His Gly Pro Gln
210                 215                 220

Glu Ser Arg Ala Val Ser Ile Ser Ile Ile Glu Pro Gly Glu Glu Gly
225                 230                 235                 240

Pro Thr Ala Gly Glu Gly Phe Asp Lys Val Arg Glu Ala Glu Asp Ser
                245                 250                 255

Pro Gln His Met
            260

<210> SEQ ID NO 16
<211> LENGTH: 246
<212> TYPE: PRT
<213> ORGANISM: Homo sapiens
<220> FEATURE:
<223> OTHER INFORMATION: Rage variant

<400> SEQUENCE: 16

```
Met Asn Arg Asn Gly Lys Glu Thr Lys Ser Asn Tyr Arg Val Arg Val
1               5                   10                  15

Tyr Gln Ile Pro Gly Lys Pro Glu Ile Val Asp Ser Ala Ser Glu Leu
            20                  25                  30

Thr Ala Gly Val Pro Asn Lys Val Gly Thr Cys Val Ser Glu Gly Ser
        35                  40                  45

Tyr Pro Ala Gly Thr Leu Ser Trp His Leu Asp Gly Lys Pro Leu Val
    50                  55                  60

Pro Asn Glu Lys Gly Val Ser Val Lys Glu Gln Thr Arg Arg His Pro
65                  70                  75                  80

Glu Thr Gly Leu Phe Thr Leu Gln Ser Glu Leu Met Val Thr Pro Ala
                85                  90                  95

Arg Gly Gly Asp Pro Arg Pro Thr Phe Ser Cys Ser Phe Ser Pro Gly
            100                 105                 110

Leu Pro Arg His Arg Ala Leu Arg Thr Ala Pro Ile Gln Pro Arg Val
        115                 120                 125

Trp Glu Pro Val Pro Leu Glu Glu Val Gln Leu Val Val Glu Pro Glu
    130                 135                 140

Gly Gly Val Val Ala Pro Gly Gly Thr Val Thr Leu Thr Cys Glu Val
145                 150                 155                 160

Pro Ala Gln Pro Ser Pro Gln Ile His Trp Met Lys Asp Gly Val Pro
                165                 170                 175

Leu Pro Leu Pro Pro Ser Pro Val Leu Ile Leu Pro Glu Ile Gly Pro
            180                 185                 190

Gln Asp Gln Gly Thr Tyr Ser Cys Val Ala Thr His Ser Ser His Gly
        195                 200                 205

Pro Gln Glu Ser Arg Ala Val Ser Ile Ser Ile Ile Glu Pro Gly Glu
    210                 215                 220

Glu Gly Pro Thr Ala Gly Glu Gly Phe Asp Lys Val Arg Glu Ala Glu
225                 230                 235                 240

Asp Ser Pro Gln His Met
                245
```

<210> SEQ ID NO 17
<211> LENGTH: 260
<212> TYPE: PRT
<213> ORGANISM: Homo sapiens
<220> FEATURE:
<223> OTHER INFORMATION: Rage variant

<400> SEQUENCE: 17

```
Met Glu Arg Arg Pro Ser Pro Thr Thr Glu Ser Val Ser Thr Ser Leu
1               5                   10                  15

Arg Thr Phe Thr Ile Thr Ala Ser Asp Trp Ile Phe Pro Pro Ser Glu
            20                  25                  30

Ile Pro Gly Lys Pro Glu Ile Val Asp Ser Ala Ser Glu Leu Thr Ala
        35                  40                  45

Gly Val Pro His Lys Val Gly Thr Cys Val Ser Glu Gly Ser Tyr Pro
    50                  55                  60

Ala Gly Thr Leu Ser Trp His Leu Asp Gly Lys Pro Leu Val Pro Asn
65                  70                  75                  80

Glu Lys Gly Val Ser Val Lys Glu Gln Thr Arg Arg His Pro Glu Thr
                85                  90                  95

Gly Leu Phe Thr Leu Gln Ser Glu Leu Met Val Thr Pro Ala Arg Gly
```

-continued

```
                100                 105                 110
Gly Asp Pro Arg Pro Thr Phe Ser Cys Ser Phe Ser Pro Gly Leu Pro
            115                 120                 125

Arg His Arg Ala Leu Arg Thr Ala Pro Ile Gln Pro Arg Val Trp Glu
        130                 135                 140

Pro Val Pro Leu Glu Glu Val Gln Leu Val Val Glu Pro Glu Gly Gly
145                 150                 155                 160

Ala Val Ala Pro Gly Gly Thr Val Thr Leu Thr Cys Glu Val Pro Ala
                165                 170                 175

Gln Pro Ser Pro Gln Ile His Trp Met Lys Asp Gly Val Pro Leu Pro
            180                 185                 190

Leu Pro Pro Ser Pro Val Leu Ile Leu Pro Glu Ile Gly Pro Gln Asp
        195                 200                 205

Gln Gly Thr Tyr Ser Cys Val Ala Thr His Ser Ser His Gly Pro Gln
    210                 215                 220

Glu Ser Arg Ala Val Ser Ile Ser Ile Ile Glu Pro Gly Glu Glu Gly
225                 230                 235                 240

Pro Thr Ala Gly Glu Gly Phe Asp Lys Val Arg Glu Ala Glu Asp Ser
                245                 250                 255

Pro Gln His Met
            260

<210> SEQ ID NO 18
<211> LENGTH: 245
<212> TYPE: PRT
<213> ORGANISM: Homo sapiens
<220> FEATURE:
<223> OTHER INFORMATION: Rage variant

<400> SEQUENCE: 18

Met Gly Ser Pro Trp Cys Leu Met Arg Arg Gly Val Ser Val Lys Glu
1               5                   10                  15

Gln Thr Arg Arg His Pro Glu Thr Gly Leu Phe Thr Leu Gln Ser Glu
            20                  25                  30

Leu Met Val Thr Pro Ala Arg Gly Gly Asp Pro Arg Pro Thr Phe Ser
        35                  40                  45

Cys Ser Phe Ser Pro Gly Leu Pro Arg His Arg Ala Leu Arg Thr Ala
    50                  55                  60

Pro Ile Gln Pro Arg Val Trp Glu Pro Val Pro Leu Glu Glu Val Gln
65                  70                  75                  80

Leu Val Val Glu Pro Glu Gly Gly Ala Val Ala Pro Gly Gly Thr Val
                85                  90                  95

Thr Leu Thr Cys Glu Val Pro Ala Gln Pro Ser Pro Gln Ile His Trp
            100                 105                 110

Met Lys Asp Gly Val Pro Leu Pro Leu Pro Pro Ser Pro Val Leu Ile
        115                 120                 125

Leu Pro Glu Ile Gly Pro Gln Asp Gln Gly Thr Tyr Ser Cys Val Ala
    130                 135                 140

Thr His Ser Ser His Gly Pro Gln Glu Ser Arg Ala Val Ser Ile Ser
145                 150                 155                 160

Ile Ile Glu Pro Gly Glu Glu Gly Pro Thr Ala Gly Ser Val Gly Gly
                165                 170                 175

Ser Gly Leu Gly Thr Leu Ala Leu Ala Leu Gly Ile Leu Gly Gly Leu
            180                 185                 190

Gly Thr Ala Ala Leu Leu Ile Gly Val Ile Leu Trp Gln Arg Arg Gln
```

```
                195                 200                 205
Arg Arg Gly Glu Glu Arg Lys Ala Pro Glu Asn Gln Glu Glu Glu Glu
    210                 215                 220
Glu Arg Ala Glu Leu Asn Gln Ser Glu Glu Pro Glu Ala Gly Glu Ser
225                 230                 235                 240

Ser Thr Gly Gly Pro
                245

<210> SEQ ID NO 19
<211> LENGTH: 246
<212> TYPE: PRT
<213> ORGANISM: Homo sapiens
<220> FEATURE:
<223> OTHER INFORMATION: Rage variant

<400> SEQUENCE: 19

Met Asn Arg Asn Gly Lys Glu Thr Lys Ser Asn Tyr Arg Val Arg Val
1               5                   10                  15

Tyr Gln Ile Pro Gly Lys Pro Glu Ile Val Asp Ser Ala Ser Glu Leu
            20                  25                  30

Thr Ala Gly Val Pro Asn Lys Val Gly Thr Cys Val Ser Glu Gly Ser
        35                  40                  45

Tyr Pro Ala Gly Thr Leu Ser Trp His Leu Asp Gly Lys Pro Leu Val
    50                  55                  60

Pro Asn Glu Lys Gly Val Ser Val Lys Glu Gln Thr Arg Arg His Pro
65                  70                  75                  80

Glu Thr Gly Leu Phe Thr Leu Gln Ser Glu Leu Met Val Thr Pro Ala
                85                  90                  95

Arg Gly Gly Asp Pro Arg Pro Thr Phe Ser Cys Ser Phe Ser Pro Gly
            100                 105                 110

Leu Pro Arg His Arg Ala Leu Arg Thr Ala Pro Ile Gln Pro Arg Val
        115                 120                 125

Trp Glu Pro Val Pro Leu Glu Glu Val Gln Leu Val Val Glu Pro Glu
    130                 135                 140

Gly Gly Ala Val Ala Pro Gly Gly Thr Val Thr Leu Thr Cys Glu Val
145                 150                 155                 160

Pro Ala Gln Pro Ser Pro Gln Ile His Trp Met Lys Asp Gly Val Pro
                165                 170                 175

Leu Pro Leu Pro Pro Ser Pro Val Leu Ile Leu Pro Glu Ile Gly Pro
            180                 185                 190

Gln Asp Gln Gly Thr Tyr Ser Cys Val Ala Thr His Ser Ser His Gly
        195                 200                 205

Pro Gln Glu Ser Arg Ala Val Ser Ile Ser Ile Ile Glu Pro Gly Glu
    210                 215                 220

Glu Gly Pro Thr Ala Gly Glu Gly Phe Asp Lys Val Arg Glu Ala Glu
225                 230                 235                 240

Asp Ser Pro Gln His Met
                245

<210> SEQ ID NO 20
<211> LENGTH: 250
<212> TYPE: PRT
<213> ORGANISM: Homo sapiens
<220> FEATURE:
<223> OTHER INFORMATION: Rage variant

<400> SEQUENCE: 20
```

```
Met Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
            35                  40                  45

Leu Glu Trp Lys Leu Asn Thr Gly Arg Thr Glu Ala Trp Lys Val Leu
        50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
                100                 105                 110

Tyr Arg Val Arg Val Tyr Gln Ile Pro Gly Lys Pro Glu Ile Val Asp
                115                 120                 125

Ser Ala Ser Glu Leu Thr Ala Gly Val Pro Asn Lys Val Gly Thr Cys
        130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
                180                 185                 190

Met Val Thr Pro Ala Arg Gly Gly Asp Pro Arg Pro Thr Phe Ser Cys
            195                 200                 205

Ser Phe Ser Pro Gly Leu Pro Arg His Arg Ala Leu Arg Thr Ala Pro
        210                 215                 220

Ile Gln Pro Arg Val Trp Gly Glu His Arg Trp Gly Pro Gln Ala
225                 230                 235                 240

His Val Ser Thr Phe Trp Lys Ser Asp Pro
                245                 250
```

<210> SEQ ID NO 21
<211> LENGTH: 121
<212> TYPE: PRT
<213> ORGANISM: Homo sapiens
<220> FEATURE:
<223> OTHER INFORMATION: Rage variant

<400> SEQUENCE: 21

```
Met Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
            35                  40                  45

Leu Glu Trp Lys Leu Asn Thr Gly Arg Thr Glu Ala Trp Lys Val Leu
        50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
                100                 105                 110
```

```
Trp Trp Trp Ser Gln Lys Val Glu Gln
        115                 120
```

<210> SEQ ID NO 22
<211> LENGTH: 388
<212> TYPE: PRT
<213> ORGANISM: Homo sapiens
<220> FEATURE:
<223> OTHER INFORMATION: Rage variant

<400> SEQUENCE: 22

```
Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
        275                 280                 285

Pro Glu Ile Gly Pro Gln Asp Gln Gly Thr Tyr Ser Cys Val Ala Thr
    290                 295                 300

His Ser Ser His Gly Pro Gln Glu Ser Arg Ala Val Ser Ile Ser Ile
305                 310                 315                 320

Ile Glu Pro Gly Glu Glu Gly Pro Thr Ala Gly Ser Val Gly Gly Ser
                325                 330                 335

Gly Leu Gly Thr Leu Ala Leu Ala Leu Gly Ile Leu Gly Gly Leu Gly
            340                 345                 350
```

```
Thr Ala Ala Leu Leu Ile Gly Val Ile Leu Trp Gln Arg Gln Arg
            355                 360                 365

Arg Ala Glu Leu Asn Gln Ser Glu Glu Pro Ala Gly Glu Ser Ser
    370                 375                 380

Thr Gly Gly Pro
385

<210> SEQ ID NO 23
<211> LENGTH: 149
<212> TYPE: PRT
<213> ORGANISM: Homo sapiens
<220> FEATURE:
<223> OTHER INFORMATION: Rage variant

<400> SEQUENCE: 23

Met Asn Arg Asn Gly Lys Glu Thr Lys Ser Asn Tyr Arg Val Arg Val
1               5                   10                  15

Tyr Gln Ile Pro Gly Lys Pro Glu Ile Val Asp Ser Ala Ser Glu Leu
            20                  25                  30

Thr Ala Gly Val Pro Asn Lys Val Gly Thr Cys Val Ser Glu Gly Ser
        35                  40                  45

Tyr Pro Ala Gly Thr Leu Ser Trp His Leu Asp Gly Lys Pro Leu Val
    50                  55                  60

Pro Asn Glu Lys Gly Val Ser Val Lys Glu Gln Thr Arg Arg His Pro
65                  70                  75                  80

Glu Thr Gly Leu Phe Thr Leu Gln Ser Glu Leu Met Val Thr Pro Ala
                85                  90                  95

Arg Gly Gly Asp Pro Arg Pro Thr Phe Ser Cys Ser Phe Ser Pro Gly
            100                 105                 110

Leu Pro Arg His Arg Ala Leu Arg Thr Ala Pro Ile Gln Pro Arg Val
        115                 120                 125

Trp Gly Glu His Arg Trp Gly Gly Pro Gln Ala His Val Ser Thr Phe
    130                 135                 140

Trp Lys Ser Asp Pro
145

<210> SEQ ID NO 24
<211> LENGTH: 28
<212> TYPE: PRT
<213> ORGANISM: Homo sapiens
<220> FEATURE:
<223> OTHER INFORMATION: Rage fragment

<400> SEQUENCE: 24

Ser Ile Ser Ile Ile Glu Pro Gly Glu Glu Gly Pro Thr Ala Gly Ser
1               5                   10                  15

Val Gly Gly Ser Gly Leu Gly Thr Leu Ala Leu Ala
            20                  25

<210> SEQ ID NO 25
<211> LENGTH: 113
<212> TYPE: PRT
<213> ORGANISM: Mus sp.
<220> FEATURE:
<223> OTHER INFORMATION: Antibody VH sequence

<400> SEQUENCE: 25

Gln Val Gln Leu Gln Gln Ser Gly Ala Glu Leu Val Lys Pro Gly Ala
1               5                   10                  15

Ser Val Lys Leu Ser Cys Lys Thr Ser Gly Tyr Thr Phe Thr Asn Tyr
```

```
                    20                  25                  30
Tyr Ile Tyr Trp Val Ile Gln Arg Pro Gly His Gly Leu Glu Trp Ile
            35                  40                  45
Gly Glu Ile Asn Pro Ser Asn Gly Gly Thr Asn Phe Ser Glu Arg Phe
 50                  55                  60
Lys Ser Arg Ala Lys Leu Thr Val Asp Lys Pro Ser Ser Thr Ala Tyr
 65                  70                  75                  80
Met Gln Leu Ser Ser Leu Thr Ser Asp Asp Ser Ala Val Tyr Tyr Cys
                85                  90                  95
Thr Thr Asn Phe Asp Tyr Trp Gly Gln Gly Ser Thr Leu Thr Val Ser
               100                 105                 110
Ser

<210> SEQ ID NO 26
<211> LENGTH: 112
<212> TYPE: PRT
<213> ORGANISM: Mus sp.
<220> FEATURE:
<223> OTHER INFORMATION: Antibody VL sequence

<400> SEQUENCE: 26

Asp Val Leu Met Thr Gln Thr Pro Leu Ser Leu Pro Val Ser Leu Gly
 1               5                  10                  15
Asp Gln Ala Ser Met Ser Cys Arg Ser Ser Gln Asn Ile Val His Asn
                20                  25                  30
Asn Gly Asn Thr Tyr Leu Gln Trp Tyr Leu Gln Lys Pro Gly Gln Ser
            35                  40                  45
Pro Lys Leu Leu Ile Tyr Gln Val Ser Asn Arg Phe Phe Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Leu Gly Val Tyr Tyr Cys Phe Gln Gly
                85                  90                  95
Ser His Leu Pro Leu Thr Phe Gly Ala Gly Thr Lys Leu Glu Leu Lys
               100                 105                 110

<210> SEQ ID NO 27
<211> LENGTH: 112
<212> TYPE: PRT
<213> ORGANISM: Mus sp.
<220> FEATURE:
<223> OTHER INFORMATION: Antibody VH sequence

<400> SEQUENCE: 27

Gln Val Gln Leu Leu Gln Pro Gly Ala Glu Leu Val Arg Pro Gly Ala
 1               5                  10                  15
Ser Val Arg Leu Ser Cys Lys Ala Ser Gly Tyr Thr Phe Thr Ser Tyr
                20                  25                  30
Trp Ile Asn Trp Val Lys Gln Arg Pro Gly Gln Gly Leu Glu Trp Ile
            35                  40                  45
Gly Asn Ile Tyr Pro Ser Asp Ser Tyr Thr Asn Tyr Asn Gln Lys Phe
 50                  55                  60
Lys Asp Lys Ala Thr Leu Thr Val Asp Lys Ser Ser Thr Ala Tyr
 65                  70                  75                  80
Met Gln Leu Ser Ser Pro Thr Ser Glu Asp Ser Ala Val Tyr Tyr Cys
                85                  90                  95
Ala Arg Glu Gly Tyr Trp Gly Gln Gly Thr Leu Val Thr Val Ser Ala
```

```
<210> SEQ ID NO 28
<211> LENGTH: 112
<212> TYPE: PRT
<213> ORGANISM: Mus sp.
<220> FEATURE:
<223> OTHER INFORMATION: Antibody VL sequence

<400> SEQUENCE: 28

Glu Leu Val Met Thr Gln Ser Pro Leu Thr Leu Ser Val Thr Ile Gly
1               5                   10                  15

Gln Pro Ala Ser Ile Ser Cys Lys Ser Gly Gln Ser Leu Leu Tyr Ser
            20                  25                  30

Asn Gly Lys Thr Tyr Leu Tyr Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Tyr Thr Phe Gly Gly Gly Thr Lys Leu Glu Ile Lys
            100                 105                 110
```